(12) United States Patent
Siegele et al.

(10) Patent No.: US 6,557,593 B2
(45) Date of Patent: *May 6, 2003

(54) REFILLABLE AMPULE AND METHOD RE SAME

(75) Inventors: Stephen H. Siegele, Austin, TX (US); Craig M. Noah, Mountain View, CA (US); John N. Gregg, San Jose, CA (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/906,161

(22) Filed: Jul. 16, 2001

(65) Prior Publication Data

US 2002/0038676 A1 Apr. 4, 2002

Related U.S. Application Data

(63) Continuation-in-part of application No. 09/013,327, filed on Jan. 26, 1998, which is a continuation-in-part of application No. 08/485,968, filed on Jun. 7, 1998, now Pat. No. 5,711,354, which is a continuation-in-part of application No. 08/345,244, filed on Nov. 28, 1994, now Pat. No. 5,607,002, which is a continuation-in-part of application No. 08/184,226, filed on Jan. 21, 1994, now abandoned, which is a continuation-in-part of application No. 08/054,597, filed on Apr. 28, 1993, now Pat. No. 5,465,766.

(51) Int. Cl.[7] .............................................. F17C 13/00
(52) U.S. Cl. ............................. 141/63; 141/1; 141/198; 141/67
(58) Field of Search ......................... 141/63, 67, 91, 141/198, 1

(56) References Cited

U.S. PATENT DOCUMENTS

| 2,160,062 A | 5/1939 | Drake et al. |
| 2,536,273 A | 1/1951 | Gahahan |
| 2,777,914 A | 1/1957 | Brown |
| 3,419,695 A | 12/1968 | Dinkelkamp et al. |
| 3,646,293 A | 2/1972 | Howard |
| 3,731,805 A | 5/1973 | Schniers ..................... 73/313 |

(List continued on next page.)

FOREIGN PATENT DOCUMENTS

DE            1036717         8/1958

OTHER PUBLICATIONS

B/W Unifloat® Liquid Level Control Systems, New single float/mulitiple switch level sensing system provides versatile, reliable means of controlling any type of liquid, Brochure by B/W Controls, Inc.

Transfil, Chemical Refill System, brochure by Air Products and Chemicals, Inc., 8/91.

TransFill™, Chemical Refill System, Brochure by Air Products and Chemicals, Inc., Aug. 1991 Rev. 1, Schumacher, Announcing A New Era In Liquid Chemical Delivery, TransFill II™, Product Brochure by Schumacher (1969).

*Primary Examiner*—J. Casimer Jacyna
(74) *Attorney, Agent, or Firm*—William F. Ryann; Margaret Chappuis

(57) ABSTRACT

A highly reliable bulk chemical delivery system for high purity chemicals employing a manifold that ensures contamination free operation and canister change outs with a minimum of valves and tubing.

18 Claims, 13 Drawing Sheets

U.S. PATENT DOCUMENTS

| | | |
|---|---|---|
| 3,826,139 A | 7/1974 | Bachman .................... 73/311 |
| 4,056,979 A | 11/1977 | Bongort et al. ............... 73/313 |
| 4,064,755 A | 12/1977 | Bongort et al. |
| 4,134,514 A | 1/1979 | Schumacher et al. |
| 4,298,037 A | 11/1981 | Schumacher et al. |
| 4,425,949 A | 1/1984 | Rowe, Jr. |
| 4,436,674 A | 3/1984 | McMenamin et al. |
| 4,576,552 A | 3/1986 | Smith |
| 4,676,404 A | 6/1987 | Yamazaki et al. |
| 4,730,491 A | 3/1988 | Lew |
| 4,859,375 A | 8/1989 | Lipisko et al. |
| 4,976,146 A | 12/1990 | Senghaas et al. |
| 4,979,545 A | 12/1990 | Fair |
| 4,979,643 A | 12/1990 | Lipisko et al. |
| 5,038,840 A | 8/1991 | Fair |
| 5,041,267 A | 8/1991 | Randtke et al. |
| 5,069,244 A | 12/1991 | Miyazaki et al. |
| 5,079,950 A | 1/1992 | McKieman et al. |
| 5,103,673 A | 4/1992 | Sawada et al. |
| 5,137,063 A | 8/1992 | Foster et al. |
| 5,138,945 A | 8/1992 | Geatz ........................ 137/208 |
| 5,148,945 A | 9/1992 | Geatz |
| 5,285,812 A | 2/1994 | Morales |
| 5,329,963 A | 7/1994 | Jones et al. |
| 5,562,132 A | 10/1996 | Siegele et al. ............... 141/198 |

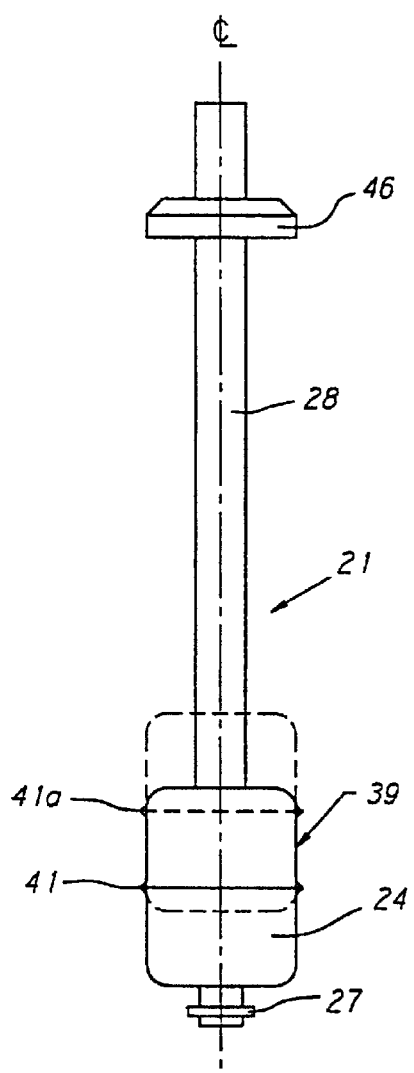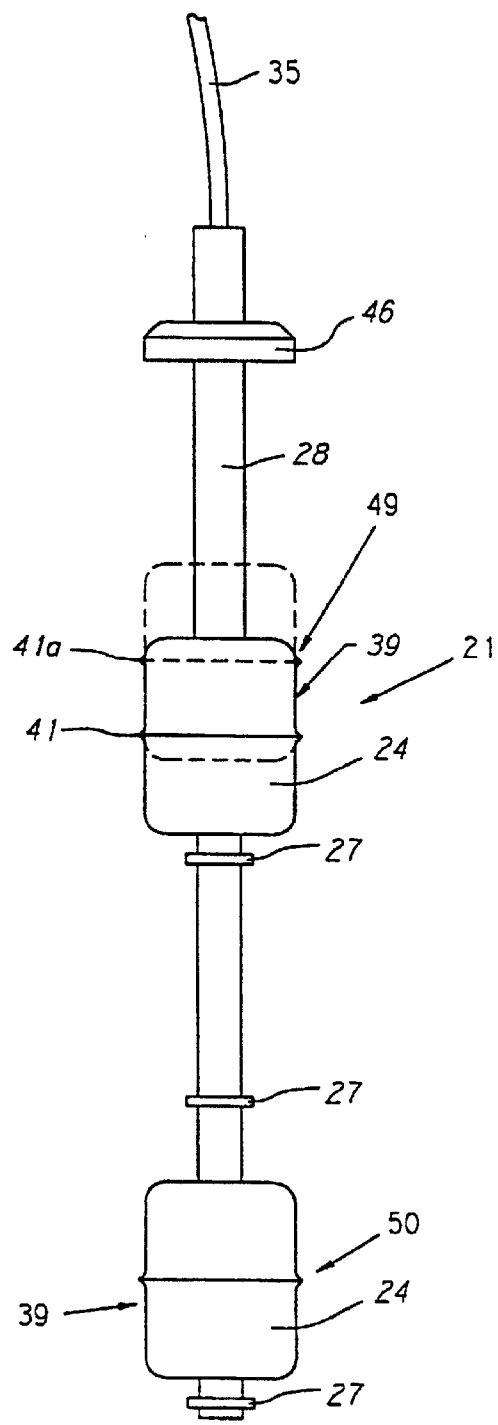
FIG. 9
FIG. 10

REFILLABLE AMPULE AND METHOD RE SAME

RELATED APPLICATIONS

This application is a Continuation-In-Part of application Ser. No. 09/013,327 filed Jan. 26, 1998, still pending, which is a CIP of Ser. No. 08/485,968, filed Jun. 7, 1995, now U.S. Pat. No. 5,711,354, which is a CIP of Ser. No. 08/345,244, filed Nov. 28, 1994, now U.S. Pat. No. 5,607,002, which is a CIP of Ser. No. 08/184,226, filed Jan. 21, 1994, now abandoned which is a CIP of Ser. No. 08/054,597, filed Apr. 28, 1993, now U.S. Pat. No. 5,465,766.

TECHNICAL FIELD OF THE INVENTION

The field of the invention relates to chemical delivery systems, in particular manifolds and level sensing schemes for chemical delivery systems, and more particularly, a highly reliable bulk chemical delivery system for high purity chemicals employing a manifold that ensures contamination free operation and canister change outs with a minimum of valves and tubing.

BACKGROUND OF THE INVENTION

The chemicals used in the fabrication of integrated circuits must have a ultrahigh purity to allow satisfactory process yields. As integrated circuits have decreased in size, there has been a directly proportional increase in the need for maintaining the purity of source chemicals. This is because contaminants are more likely to deleteriously affect the electrical properties of integrated circuits as line spacing and interlayer dielectric thicknesses decrease.

One ultrahigh purity chemical used in the fabrication of integrated circuits is tetraethylorthosilicate (TEOS). The chemical formula for TEOS is $(C_2H_5O)_4Si$. TEOS has been widely used in integrated circuit manufacturing operations such as chemical vapor deposition (CVD) to form silicon dioxide films. These conformal films are generated upon the molecular decomposition of TEOS at elevated temperatures and reduced pressures (LPCVD), or at lower temperatures in plasma enhanced and atmospheric pressure reactors (PECVD, APCVD). TEOS is typically used for phosphorous undoped and bottom doped interlayer dielectrics, intermetal dielectrics, sidewall spacers and trench filling applications.

Integrated circuit fabricators typically require TEOS with 99.999999+% (8–9's+%) purity with respect to trace metals. Overall, the TEOS must exhibit a 99.99+% purity. This high degree of purity is necessary to maintain satisfactory process yields. However, it also necessitates the use of special equipment to contain and deliver the high purity TEOS to the CVD reaction chamber.

Traditionally, high purity TEOS has been fed to the CVD reaction chamber from a small volume container called, an ampule. Historically, it was strongly believed ampules could not be metallic and that no metal should interface with the high purity TEOS or other source chemicals in the ampule. The use of metal ampules was spurned in the industry on the basis of the belief that high purity TEOS and other high purity source chemicals used in the semiconductor fabrication industry would pick up contamination from the metallic container in the form of dissolved metal ions. Thus, the industry used, almost exclusively, quartz ampules.

When these relatively small quartz ampules were emptied, they would simply be replaced with a full ampule. The ampules were not refilled in the fabrication area. The empty ampule was returned to the chemical manufacturer who would clean and refill the ampule.

Inconveniences resulting from the use of the quartz ampules are that they require frequent replacement due to their small size, which increases the potential for equipment damage. Furthermore, quartz ampules are subject to breakage, and have limited design versatility. Also, quartz has limited heat capacity making it difficult to control temperature of the ampule. Plus, the lack of effective quartz-to-stainless steel seals created significant leak problems.

In an attempt to solve the problem associated with quartz ampules, at least one supplier of ultrahigh purity chemicals, Advanced Delivery & Chemical Systems, Inc., going against the belief in the industry that high purity source chemicals should not be placed in contact with metal, developed a stainless steel ampule. This ampule was used to directly supply high purity TEOS and other high purity source chemicals to semiconductor fabrication equipment. As with the quartz ampules, when it was empty it was not refilled, but rather returned to the supplier for cleaning and refilling.

There were still several problems with using the stainless steel ampule. Namely, because of the small size of the these ampules, they often required frequent replacement. Also, an optical sensor employing a quartz rod was used to detect when the high purity TEOS reached a low level inside the ampule. Unfortunately, optical sensors, which employ a light emitting diode and a photodetector in combination with a quartz rod, require a high degree of maintenance because they are subject to misalignment if jostled. Furthermore, the conditioning circuit of the sensor must be constantly tuned because the sensor is subject to calibration drift, which can cause false sensor output signals. These problems can result in allowing the ampule to run dry or causing the premature removal of a partial or full ampule. Another problem with optical sensors is that they are prone to breakage in transport and cleaning, requiring frequent replacement. Despite these problems, optical sensors were used over more reliable metallic float sensor systems because of the fears of contaminating the high purity chemical with metal particles and metal ions.

In an attempt to solve the problem of frequent replacement of stainless steel ampules, a larger five gallon stainless steel tank was developed to refill the smaller stainless steel ampule. This tank also used an optical level sensor to detect when the container had been depleted, despite all of the problems associated with optical level sensors. Like the ampule in the previous configuration, this tank was not refilled, but was rather returned to the supplier for cleaning and refilling. Due to the size and weight of the five-gallon tank, it is subject to more physical jarring than the smaller ampules when transported and changed out with empty canisters, thus causing a higher frequency of problems with the traditional optical sensors used to detect a low level of source chemical in the delivery system.

Furthermore, in this refill configuration a second optical sensor, with all of the problems associated with such sensors, was required in the ampule to signal when the ampule was full during the refilling process. This, in some cases, required another opening in the ampule which is undesirable, because this introduces additional potential for leaks and contamination points.

In an attempt to overcome the problems associated with the optical sensors, a metallic level sensor was employed to detect low levels of high purity chemicals in the five-gallon bulk container. The metallic level sensor generally consisted of a toroidal shaped float made of stainless steel held captive on a hollow shaft made of electropolished stainless steel. The float contained a fixed magnet. A digital reed relay was secured at a fixed position inside the shaft at an alarm trigger point. As the float travelled past the reed relay, the fixed magnet would change its state, thus causing a low level alarm condition to be signaled. A replacement tank would then be substituted. The digital magnetic reed relay used in the metallic float level sensor provided much more reliable detection of low source chemical levels in the remote tank, because the magnetic reed switch is a low maintenance mechanical switch and provides positive on/off switching. As before, the empty 5-gallon container was never refilled by the user. It was always returned to the chemical supplier for cleaning and filling.

A low level metallic float sensor has also been used more recently in the stainless steel ampule. Due to fears associated with contamination, however, the ampules were not refilled by the user and were only used in stand alone systems. As with the five-gallon tank, when the metallic level sensor indicated the high purity TEOS or other high purity source chemical level was low, the ampule was simply replaced with a full ampule. In no instance was a metallic level sensor used to detect the level of high purity TEOS or other high purity source chemical in an ampule when the ampule was used in any refill type system. Ampules used in refill type systems have not used a float-type sensor or any other sensor with movable parts.

The use of metallic level sensors has been spurned in ampules used in refill type systems because of the strong belief in the industry that sliding metal to metal contact will cause the shedding of metal particles and dissolution of metal ions, thus contaminating the high purity TEOS or other high purity source chemical employed in the delivery system. This belief exists despite the use of low level metal float sensors in stand alone stainless steel five-gallon tanks and in stainless steel ampules. This is because in the stand alone systems, the tank or ampule is exchanged with a replacement tank or ampule, respectively, following each use. Furthermore, following each use, the tank or ampule is cleaned before refilling for a subsequent use. Both the cleaning and refilling are accomplished at a remote location by the supplier of the source chemical. Therefore, the amount a metal float travels in a stand alone system is limited to one fill and drain cycle. On the other hand, in a refill system the ampule is periodically refilled from a remote bulk container after each time it is emptied. Further, in a refill system, the ampule is never completely drained of high purity TEOS or other high purity source chemical between each refilling. Thus, integrated circuit manufacturers and source chemical suppliers have had an unsubstantiated concern that with repeated fillings of the same ampule over a period of time, the metal ion concentration and metal particles in the ampule would increase to an unacceptable level. As a result of this concern, ampules that have been used in refill type systems have always been equipped with the optical sensors or with sensors with non-movable parts, despite the knowledge that metallic float level sensors were much more reliable in refill systems.

Because, as noted above, optical sensors require a high degree of maintenance and are subject to frequent failure, the reliability of the bulk chemical refill systems using optical sensors have been in question. When the optical sensor fails to detect a low or "empty" level, the ampule can be ran dry during the CVD process. As previously discussed, this could destroy the batch of wafers then in process or force their rework at a cost of thousands to tens of thousands of dollars. On the flip side, when the optical sensor fails to detect the high or "full" level during a refill cycle, the ampule can be overfilled potentially causing damage to costly equipment; wasting expensive high purity source chemical (high purity TEOS costs approximately $2,000/gal.); contaminating the fabrication area, which is typically a class 1 or class 10 clean room environment; contaminating or damaging other equipment in the clean room; ruining the wafers being processed; and causing severe personal safety concerns. In the past, to avoid these problems semiconductor equipment manufacturers have used refill systems with redundant optical level sensors to minimize the impact of sensor malfunctions, used other level sensor types, excluding float type sensors described, employed a timed refill, the refill of a small fixed volume or the refill of a measured mass of chemical. These refill systems suffer characteristic performance problems arising from: non-linearity of alternate sensor technology, uncertainty of the refill volume, the lack of a positive shut-off of the chemical fill, the risk of malfunction due to maladjustment of system components or the lack of level monitoring of the bulk chemical source. Therefore, a need exists for a reliable bulk chemical refill system for applications where a high degree of chemical purity must be maintained, and a high level or error free refill confidence must exist.

SUMMARY OF THE INVENTION

The present invention provides manifolds and level sensing schemes for chemical delivery systems, and more particularly, a highly reliable bulk chemical delivery system for high purity chemicals employing a manifold that ensures contamination free operation and canister change outs with a minimum of valves and tubing. The present invention substantially eliminates or reduces disadvantages and problems associated with previously developed level sensing schemes for chemical delivery systems.

Accordingly, it is an object of the present invention to provide a bulk chemical delivery system for among other chemicals, high purity chemicals of the type described above, but which uses a highly reliable manifold and method for using the manifold in a bulk chemical delivery system.

Through the unique set up of piping and valves and their method and sequence of operation, bulk canisters can be replaced without fear of contamination. This is especially useful in refillable high purity chemical bulk delivery systems.

The above and other objects, features and advantages of the invention will become apparent from the following detailed description of the preferred embodiments, taken in conjunction with the accompanying drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 9 is a side view of a metallic level switch assembly for a refillable container according to a preferred embodiment of the present invention;

FIG. 10 is a side view of metallic level switch assembly for a refillable container according to another embodiment of the present invention;

FIG. 18 is a schematic view of a manifold layout for the preferred embodiment of the present invention.

DETAILED DESCRIPTION OF THE INVENTION

Preferred embodiments of the present invention are illustrated in the FIGUREs, like numerals being used to refer to like and corresponding parts of the various drawings.

Figure 1:
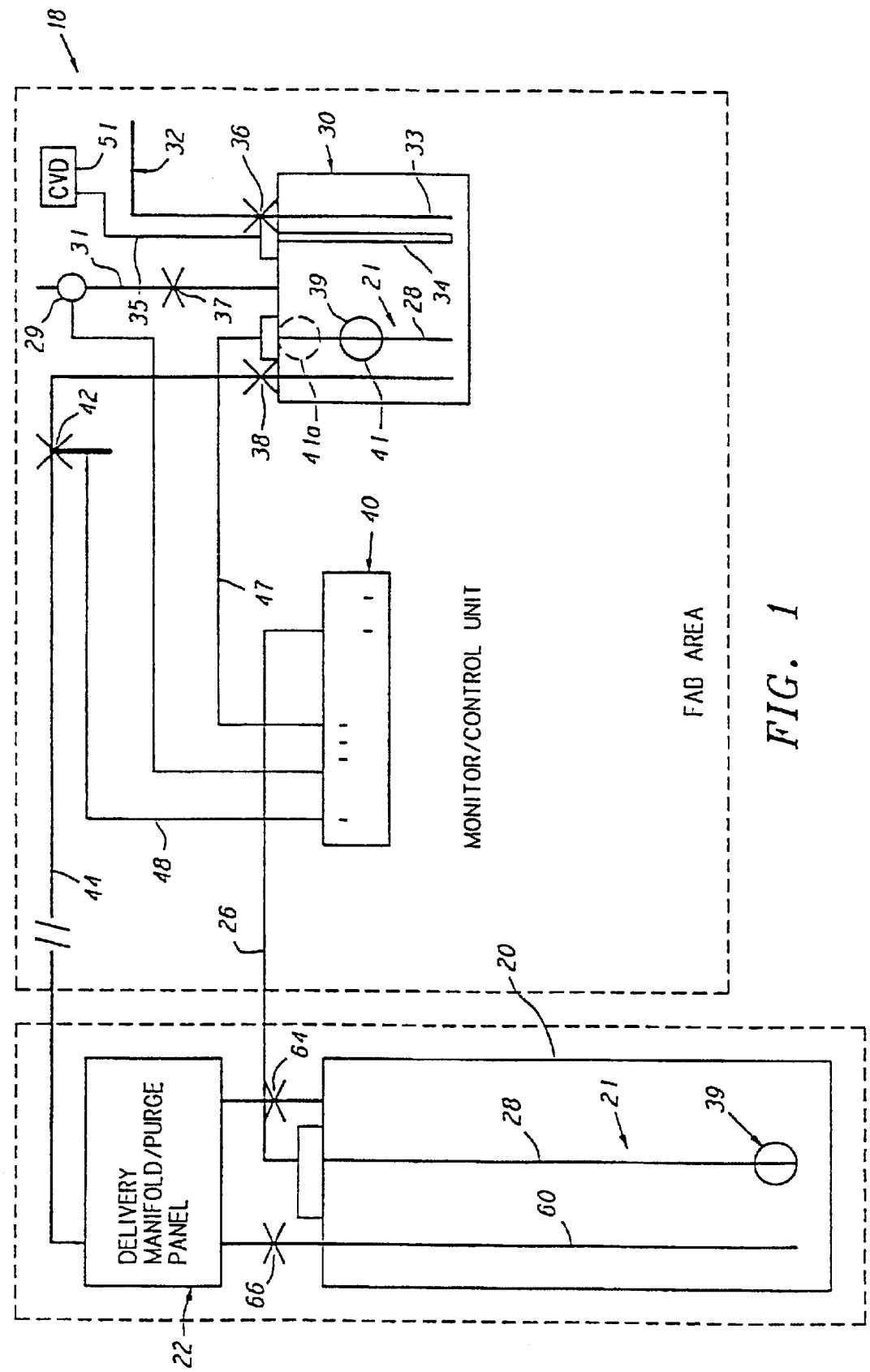
FIG. 1 is a schematic representation of a high purity chemical refill delivery system according to one embodiment of the present invention.

A preferred embodiment of a high purity chemical refill system is described in connection with FIG. 1. The system consists of three main functional components: a bulk canister 20 located in a remote chemical cabinet with a delivery manifold/purge panel 22; a refillable stainless steel ampule 30 to supply semiconductor fabrication equipment such as a CVD reactor with high purity TEOS or other high purity source chemicals; and a control unit 40 to supervise and control the refill operation and to monitor the level of the bulk container.

Bulk chemical refill system 18 has two basic modes of operation: a normal process operation and a refill mode of operation. Under normal process operation, refillable ampule 30 delivers high purity TEOS or other high purity source chemicals to semiconductor fabrication equipment fabrication equipment via outlet passage 32. Outlet passage 32 is connected to the semiconductor processing equipment using conventional process connections.

Figure 13:
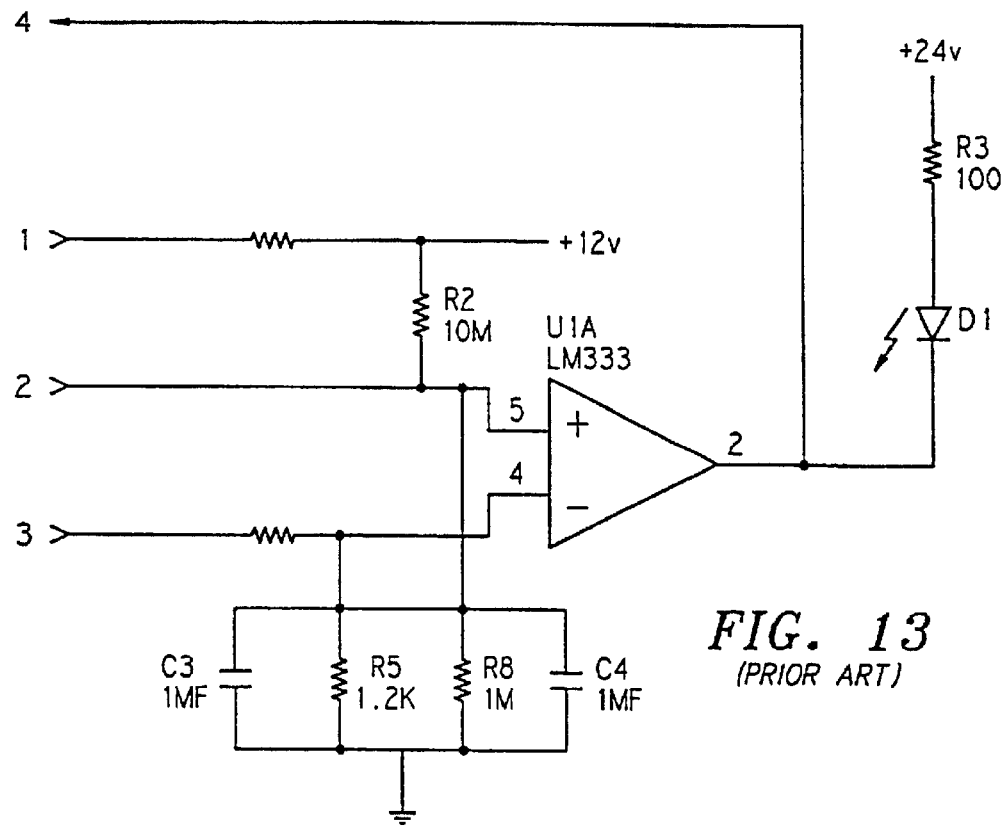
FIG. 13 is a schematic diagram of typical prior art conditioning circuitry for interfacing an optical level sensor with existing semiconductor processing equipment.

In this embodiment the refillable ampule 30 incorporates an optical sensor 34 for communicating a low level signal to the CVD reactor through the conventional low level sensor/reactor interface circuit shown in FIG. 13. When a low level signal is communicated to the fabrication equipment, the equipment will employ the signal in accordance with its normal conventional operation, such as its normal low level default procedure.

Figure 2:
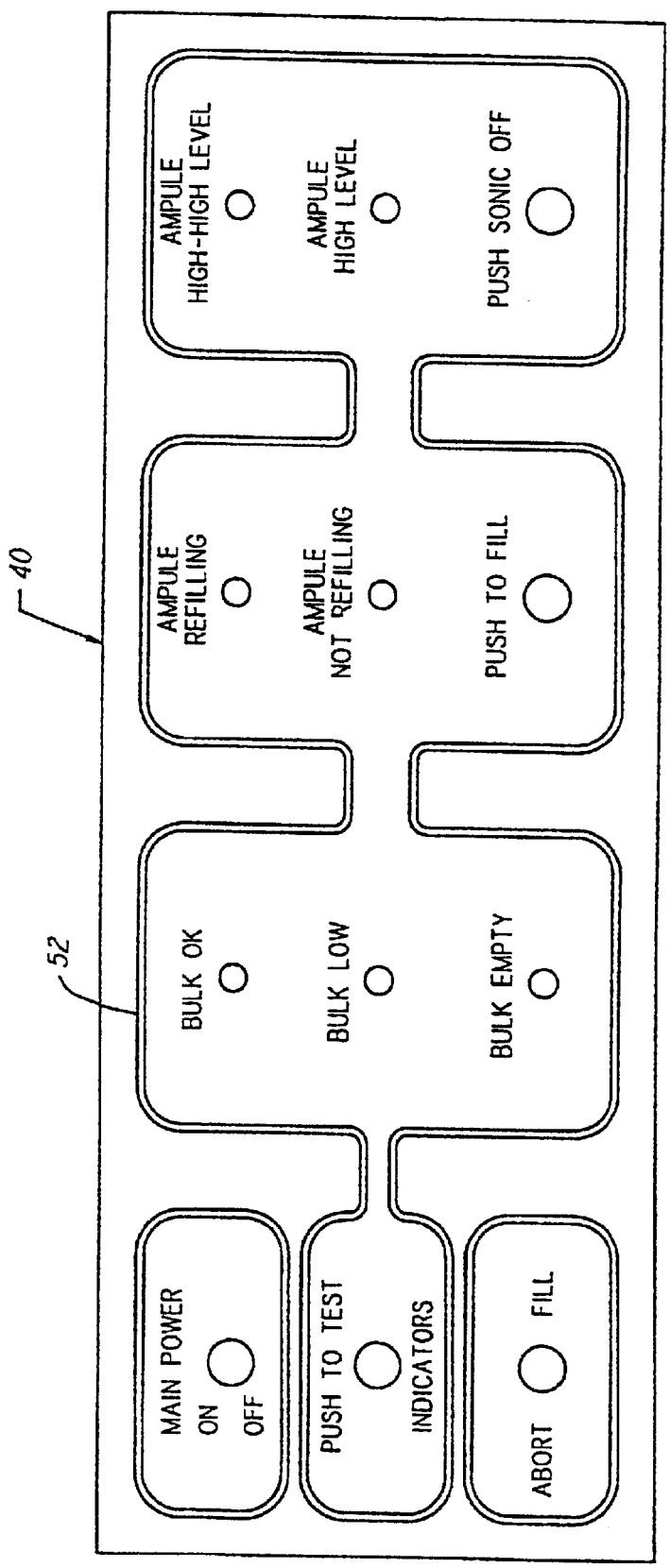
FIG. 2 is a front view of a control unit control panel according to one embodiment of the present invention.

FIG. 2 illustrates a preferred arrangement of control panel 52 of control unit 42. Control panel 52 contains five switches: a "MAIN POWER" on off switch, a "PUSH TO TEST INDICATORS" switch, an "ABORT FILL" switch, a "PUSH TO FILL" switch, and a "PUSH SONIC OFF" switch. The operation of these switches is described in detail in conjunction with FIGS. 15, 15A and 15B below.

Control panel 52 also includes a number of illuminated indicators to report the status of chemical levels in bulk container 20 and ampule 30. The illuminated indicators include "BULK OK", "BULK LOW", "BULK EMPTY", "AMPULE REFILLING", "AMPULE NOT REFILLING", "AMPULE HIGH—HIGH LEVEL", and "AMPULE HIGH LEVEL".

A preferred method of operation of control unit 40 during normal process operation is described in connection with FIG. 2. During normal process operation, the level of source chemical in bulk container 20 should not change. Therefore, the "BULK OK" indicator should remain lit. However, if the "BULK LOW" or "BULK EMPTY" indicator came on during the last refill cycle, these indicators will remain illuminated until the bulk container 20 is replaced with a full container. The operation of the level sensors in bulk container 20 is explained in more detail below.

Throughout normal process operation, the "AMPULE NOT FILLING" indicator should remain on to indicate that the refill system is not in the refill mode. Because the level of high purity TEOS or other high purity source chemical in refillable ampule 30 changes throughout normal process operation, the "AMPULE HIGH" level indicator, which is illuminated upon completion of a refill cycle, will remain illuminated until the high purity TEOS or other high purity source chemical level in refillable ampule 30 falls below the "AMPULE HIGH" trigger point 41 of metallic level sensor 39.

It should be noted that if the "AMPULE HIGH—HIGH" indicator was illuminated during the refill process, as with the "AMPULE HIGH" indicator, the "AMPULE HIGH—HIGH" indicator will remain on until the high purity source chemical in ampule 30 falls below the "HIGH—HIGH" trigger point 41a of metallic level sensor 39. In such a case, the chemical level will fall through the "AMPULE HIGH" trigger region thus causing the "AMPULE HIGH" indicator to illuminate and then extinguish as described above.

The refill procedure is started either automatically or semiautomatically. The semiautomatic procedure begins by the operator manually configuring ampule 30 to the refill configuration. This is done by closing the outlet valve 36 on the ampule 30. In addition, the operator would verify that the inlet valve 38 is closed.

Because the high purity TEOS or other high purity source chemical is supplied under pressure to some CVD reactors by an inert gas such as He during normal operation, the ampule 30 may need to be depressurized and a vacuum pulled to ease the high purity TEOS or other high purity source chemical transfer process. The depressurization and degassing process are accomplished using standard techniques utilized in the chemical vapor deposition art through passage 31. After the depressurization step, the vacuum/pressurization valve 37 is closed. Inlet valve 38 is now opened to allow the flow of high purity TEOS or other high purity source chemical into ampule 30. The pressurization would be unnecessary for other applications where pressurization of the headspace of ampule 30 would not present a problem.

The semiautomatic refilling process requires an operator to depress the "PUSH TO FILL" switch on control panel 52 of control unit 40 shown in FIG. 2. Once the "PUSH TO FILL" switch is pushed, the control unit 40 opens a valve 42 in the refill line 44. High purity TEOS or other high purity source chemical, depending on the application, then flows into the ampule 30 from the bulk container 20.

Valve 42 is preferably a pneumatically activated valve. When a pneumatically activated valve is used for valve 42, it is opened when a control pressure is supplied through passage 46 from control unit 40. The control pressure used to open valve 42 can be nitrogen or other pressurization gas such as plant compressed dry air. The flow of a control pressure through passage 46 is controlled by solenoid valves in control unit 40. The operation of these solenoid valves is described in detail below in conjunction with FIGS. 15, 15A and 15B.

Bulk container 20 is continuously pressurized with an inert gas such as helium; thus, when valve 42 is opened, inert gas forces the high purity source chemical from bulk container 20 through refill line 44 and to the ampule 30.

Metallic level sensor assembly 21 in ampule 30 contains a high level metallic level sensor 39. Metallic level sensor 39 is preferably a dual level sensor capable of detecting two separate levels of source chemical in ampule 30. However, metallic level sensor 39 can also be a single level sensor, or a multiple trigger point level sensor up to a continuous level sensor. In the preferred embodiment metallic level sensor 39 is a dual level sensor with two trigger points, 41 and 41a. Trigger point 41 is for detecting a "HIGH LEVEL" (full) condition in ampule 30, and trigger point 41(a) detects a "HIGH—HIGH LEVEL" condition in ampule 30.

When the metallic level sensor 39 detects that the ampule 30 is full, it supplies a signal to the control unit 40 via cable 47. In response to that signal control unit 40 closes pneumatic valve 42 without operator intervention. Simultaneously, control unit 40 signals an audible and visual alarm on control panel 52. If the "HIGH LEVEL" trigger point 41 of metallic level sensor 39 should fail, the "HIGH—HIGH LEVEL" trigger point 41a of metallic level sensor 39 is in place and will trigger and instruct control unit 40 that the ampule 30 is full via cable 47 by an independent circuit within the control unit 40. This "HIGH—HIGH" alarm is a fail safe feature that prevents overfilling the ampule 30 and stops refilling in case of electrical failure of the "HIGH LEVEL" alarm circuit and is described below in connection with FIGS. 15, 15A and 15B. Obviously, if metallic level sensor 39 is only a single level sensor, only a "HIGH LEVEL" condition can be detected, and no fail safe level detection is provided. Additionally, when the metallic level sensor 39 detects that the ampule 30 is at a low level, such as at trigger points described below, a signal may be supplied to the control unit 40 to open the pneumatic valve 42 with or without operator intervention.

Control unit 40 also interfaces with a metallic level sensor assembly 21 in bulk container 20 via cable 26. The metallic level sensor 39 in the remote bulk container has its trigger points preferably set at 20% remaining source chemical and at 5% remaining source chemical. Depending on specific process requirements, however, other trigger points can be used. If the source chemical level falls below the first trigger point, which typically only occurs during the refilling sequence, a visual indication of "BULK LOW" on the control panel 52 of control unit 40 is produced. If the source chemical level falls below the second trigger point, a "BULK EMPTY" visual alarm on control panel 52 in addition to an audible alarm is produced in conjunction with an automatic termination of the refill sequence.

Control unit 40 can also be configured for manual shut off during the refill cycle. In such a configuration, the operator would terminate the refill cycle by manually depressing a button on control panel 52 upon acknowledging a visual or audible indication that the refillable ampule 30 is full. Similarly, a fully automatic start/automatic shut off configuration can be provided. This can be accomplished by replacing manual vacuum/pressurization valve 37 with an automatic valve preferably pneumatic, and placing a pressure sensor in the passage 31 to ampule 30. The pneumatic valve and pressure sensor are then connected to control unit 40. When a specified vacuum is pulled on ampule 30 at the beginning of the refill cycle to ease the flow of high purity source chemical into ampule 30, the pressure sensor in passage 31 would signal control unit 40. In response, control unit 40 would close the pneumatic valve 37 and simultaneously open pneumatic valve 42 in the refill line 44, thus automatically initiating the refill process.

Figure 3:
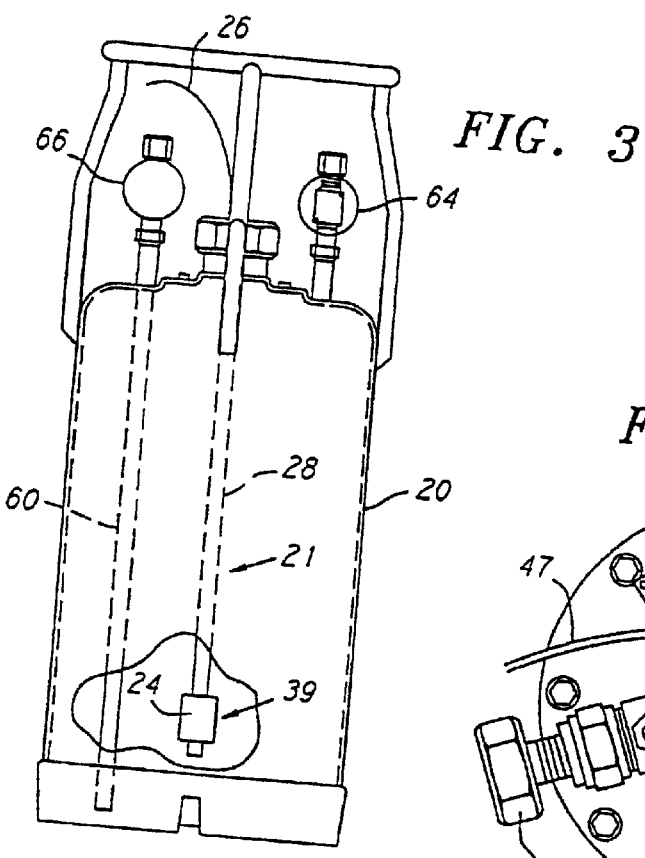
FIG. 3 is a side view in partial cross section of a five-gallon high purity chemical container.

A particularly preferred bulk container 20 will now be described in connection with FIG. 3. Bulk container 20 is made of 316L electropolished stainless steel to minimize the risk of contamination to the high purity source chemical contained within the tank. Bulk container 20 typically comes in a five-gallon capacity. However, larger capacity canisters can be used for bulk container 20, including ten and twenty-gallon containers. Smaller containers may be used too, for example, one and two-gallon containers. Bulk container 20 is used to supply a bulk high purity source chemical such as high purity TEOS from a remote location to ampule 30. The source chemical is delivered by continuous pressurization of the canister with inert gas such as helium for on demand refill of the refillable ampule 30. The inert gas is supplied through the inlet valve 64. Inlet valve 64 is connected to and communicates with passage 88 of the delivery/purge manifold 22 which is in communication with an inert gas source. The outlet valve 66 also connects to the refill line 44 by way of manifold 22. Thus when container 20 is pressurized with helium gas or another suitable gas and pneumatic valve 42 is opened, high purity TEOS or other high purity source chemical is forced through outlet pipe 60, outlet valve 66, manifold 22, refill line 44, inlet valve 38 and into refillable ampule 30.

In one embodiment, bulk container 20 is provided with a metallic level sensor assembly 21 including a metallic level sensor 39 preferably comprised of a two pole reed switch triggered by a metallic float 24. It is understood that other types of triggers, such as a Hall effect sensor may be employed. The two-pole reed switch interfaces directly with control unit 40 through cable 26. Metallic level sensor 39 preferably is a dual level sensor, in that it incorporates two reed switches. As with the metallic level sensor 39 in refillable ampule 30, however, it can incorporate any desirable number of reed switches to detect one or more levels of source chemical. Further any number of separate metallic level sensors 39, each employing their own metallic float 24 may be employed.

The principle of operation behind metallic level sensor 39 is described in connection with the single level metallic level sensor 39 illustrated in FIGS. 4 and 5. Metallic level sensor 39 is comprised of a toroidal shaped metallic float 24 made of stainless steel or other non-magnetic, chemically inert material. Alternatively, metallic float 24 is coated with a fluoropolymer or other chemically inert coating. The preferred construction material is 316L stainless steel. Metallic float 24 contains a fixed magnet 23 and is held captive on a hollow metallic shaft 28. Shaft 28, however, is sealed on its bottom and extending into ampule 30 to prevent high purity source chemical from flowing up into the shaft. Further, metallic shaft 28 is preferably made of electropolished 316L stainless steel or other chemically inert material. Alternatively, shaft 28 is made of a non-magnetic material coated with a fluoropolymer or other chemically inert material. Inside shaft 28, a digital magnetic reed relay switch RS is secured in a fixed position at a predetermined alarm trigger point. This trigger point corresponds, for example, to the "BULK EMPTY" trigger set point. A ferrule 46 is permanently attached to one end of shaft 28 for attachment to the container.

Additional reed relay switches RS may be added within shaft 28 to form a multiple level detector. For example, if a second reed relay switch RS is added at second fixed trigger point within shaft 28 a dual level float sensor is created. Additional reed relay switches RS may be added for any number of additional levels of detection.

Retainer rings 27 are used to restrain the movement of the metallic float 24 so that upon filling of bulk container 20, the float is restrained from sliding up the entire length of shaft 28, and sliding back down the entire length of shaft 28 as bulk container 20 is drained. It should be noted that, if desired the upper retainer ring 27 may be eliminated in this configuration. Only the lower retainer ring 27 is necessary to prevent metallic float 24 from sliding off shaft 28. Retainer rings 27 are also preferably constructed from 316 stainless steel, Kalrez.™. or other suitable, chemically inert material.

Metallic level sensor assembly 21 comprising shaft 28, metallic float 24 and retainer ring 27 is preferably electropolished following assembly. In addition, the surface finish of all wetted metal parts is preferably Ra 20 or better prior to electropolishing.

Metallic level sensor 39 works as follows, when the liquid source chemical is above the upper retainer ring, the metallic float 24 remains at the top ring 74 in the "float up" position. As the liquid level drops, metallic float 24 moves down the shaft 28. When the magnetic field from fixed magnet 23 latches the magnetic reed switch RS, metallic float 24 is in the "float down" position. When the magnetic reed switch is closed, the indicator circuit is completed. This output signal is transmitted through one of two wires 25 in cable 26 to an alarm circuit in control unit 40.

Figure 4:
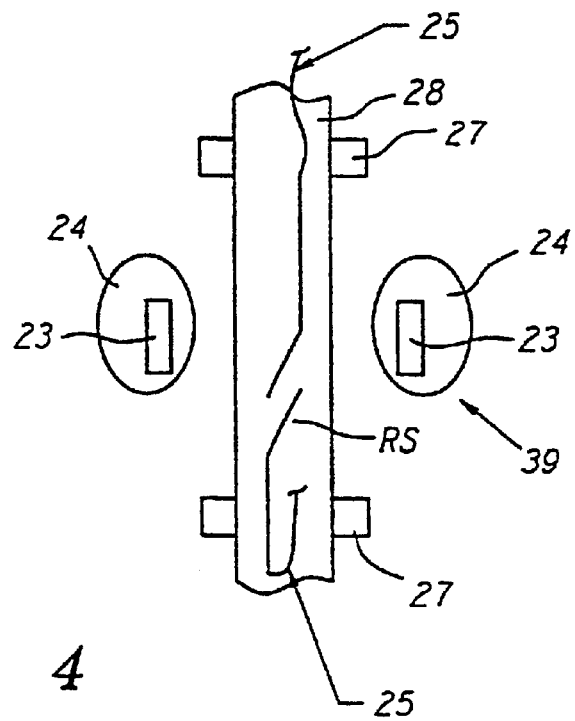
FIG. 4 is a schematic representation of a single level float control sensor in the "open" position of one embodiment.
Figure 5:
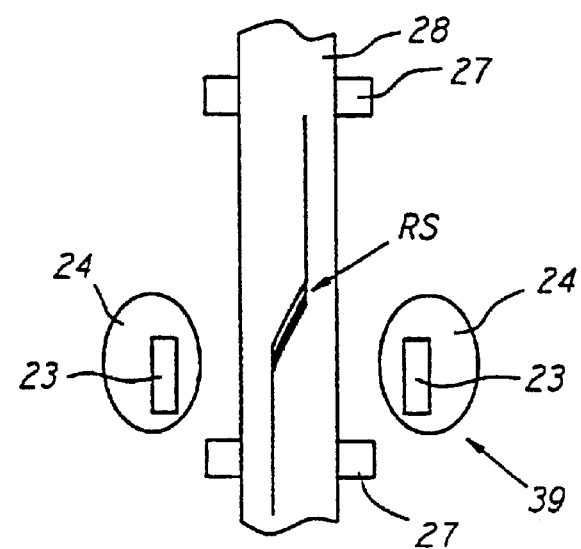
FIG. 5 is a schematic representation of a single level float level sensor in the "closed" position of one embodiment of the present invention.

FIGS. 4 and 5 illustrate the use of a normally open magnetic reed switch RS. Alternatively, however, a normally closed magnetic reed switch can be used. In such a case, as the metallic float 24 travels pass the reed relay, the fixed magnet 23 will open the reed relay switch RS. Thus, the alarm condition is signaled either by opening the closed relay contacts or by closing the open reed relay contacts.

As discussed above, in the preferred embodiment, a dual level metallic sensor 39 is utilized. A dual level metallic sensor 39 is provided simply by securing a second digital magnetic reed relay switch RS at a desired alarm trigger point. The single metallic float 24 on shaft 28 can trigger both reed switches. If a dual level metallic sensor is used, four wires are found in cable 27 and are used to communicate the state of the switches to the control unit 40. Preferably, the second trigger point should be set for 20% source chemical remaining. In the preferred embodiment, this corresponds to the "BULK LOW" trigger point.

A second sensor configuration could incorporate a fixed magnet 23 inside a float made of the same materials as metallic float 24 and attached to shaft 28 by means of a hinge. As the float swivels, it brings the fixed magnet into proximity of a reed relay switch RS and changes the state of the reed relay from open to closed or closed to open.

Figure 7:
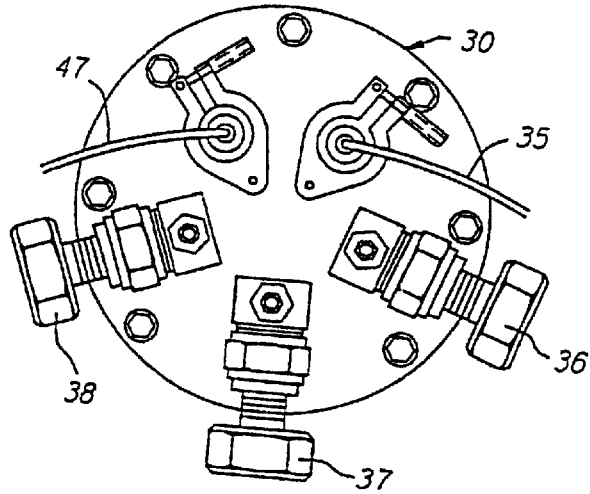
FIG. 7 is a top view of the ampule illustrated in FIG. 6.
Figure 6:
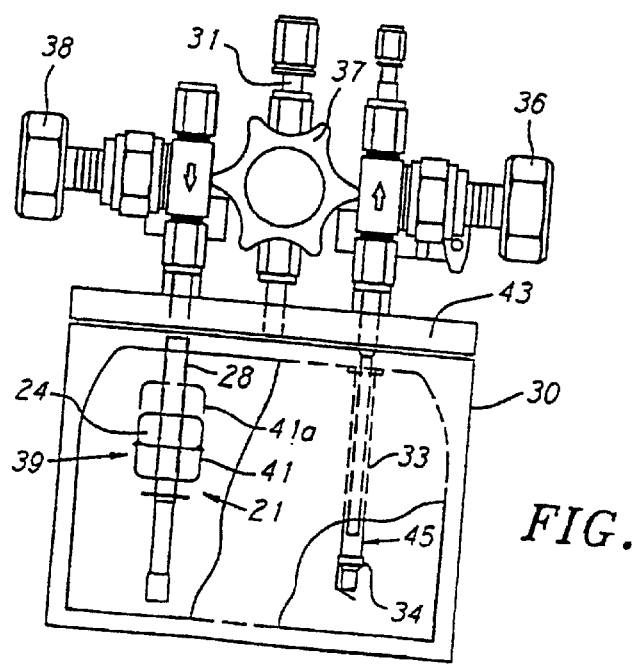
FIG. 6 is a side view in partial cross-section of a refillable ampule according to one embodiment of the present invention.

Refillable ampule 30 can now be described in connection with FIGS. 6 and 7. Refillable ampule 30 is preferably made from 316L electropolished stainless steel construction. Typically, ampule 30 has a 2.3 liter capacity, but can be provided in a wide range of sizes, including 1.3 liter, 1 gallon, 1.6 gallons, 2 gallons, and 5 gallons. The size of the ampule merely depends on process demands.

Vacuum/pressurization valve 37 permits refillable ampule 30 to be pressurized with an inert gas such as helium during normal process operation, which is typical of many CVD ampules. This valve also has the function of permitting the depressurization and application of a vacuum to ampule 30 prior to a refill sequence or removal of ampule 30 from the system 18.

Outlet valve 36 connects refillable ampule 30 to a delivery line 32 that supplies liquid high purity TEOS or other high purity source chemical directly to the semiconductor processing equipment during normal process operation. Thus, during normal process operation, helium or other inert pressurizing gas is supplied through vacuum/pressurization valve 37 to pressurize ampule 30. The pressure applied to the internal cavity of ampule 30 forces high purity TEOS or other high purity source chemical through hollow pipe 33 and outlet valve 36 to delivery line 32 that feeds a CVD reaction chamber. It should be noted that the entirety of pipe 33 is not shown on the drawing to allow the optical sensor assembly 45 to be seen. Normally the pipe 33 extends below the end of the optical sensor 34 to allow for proper operation of the system.

Figure 14:
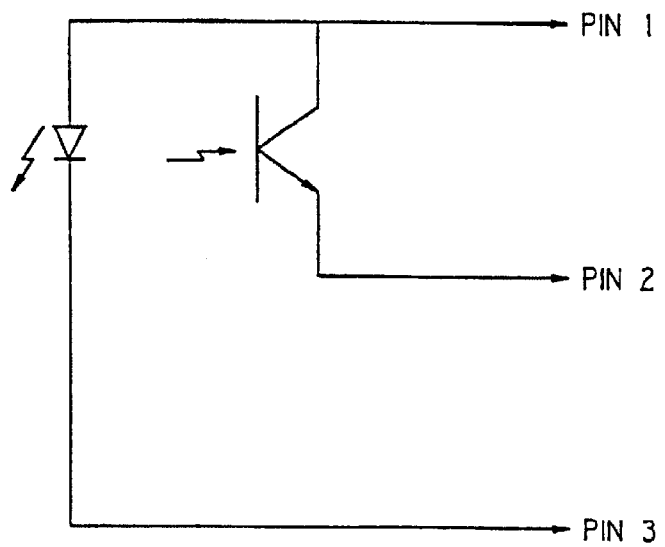
FIG. 14 is an electrical schematic diagram of a prior art optical level sensor.

In the depicted embodiment, low level sensor 34 is an optical sensor. It is of the type commonly used with standard CVD processing equipment, and need not be explained in detail. An electrical schematic diagram of the optical sensor 34 is illustrated in FIG. 14. Low level optical sensor 34 sends signals through cable 35 to an independent alarm module, the display panel for the reactor itself, or through a temperature controller, but not through control panel 40. Because low level sensor 34 is an optical sensor in the present embodiment of the invention, it can interface with the semiconductor processing equipment, independent alarm module or temperature controller using the existing circuitry illustrated in FIG. 13 for interfacing a low level optical sensor with a reactor, independent alarm module, or temperature controller.

Inlet valve 38 is a manual shut-off valve for the refill line 44. Valve 38 remains closed during normal process operation and is opened only during a refill sequence. In the fully automatic process this is an automatic valve, preferably pneumatically activated.

Metallic level sensor assembly 21 contains at least a single level metallic sensor level 39. Preferably, however, metallic level sensor 39 is a dual level sensor for detecting "HIGH LEVEL" and "HIGH—HIGH LEVEL" respectfully. The metallic level sensor 39 of the metallic level sensor assembly 21 operates in the same manner as described in connection with FIGS. 4 and 5. Metallic level sensor 39 illustrated in FIG. 6 is a dual level sensor with trigger points at "HIGH LEVEL" 41 and "HIGH—HIGH LEVEL" 41a.

Figure 8:
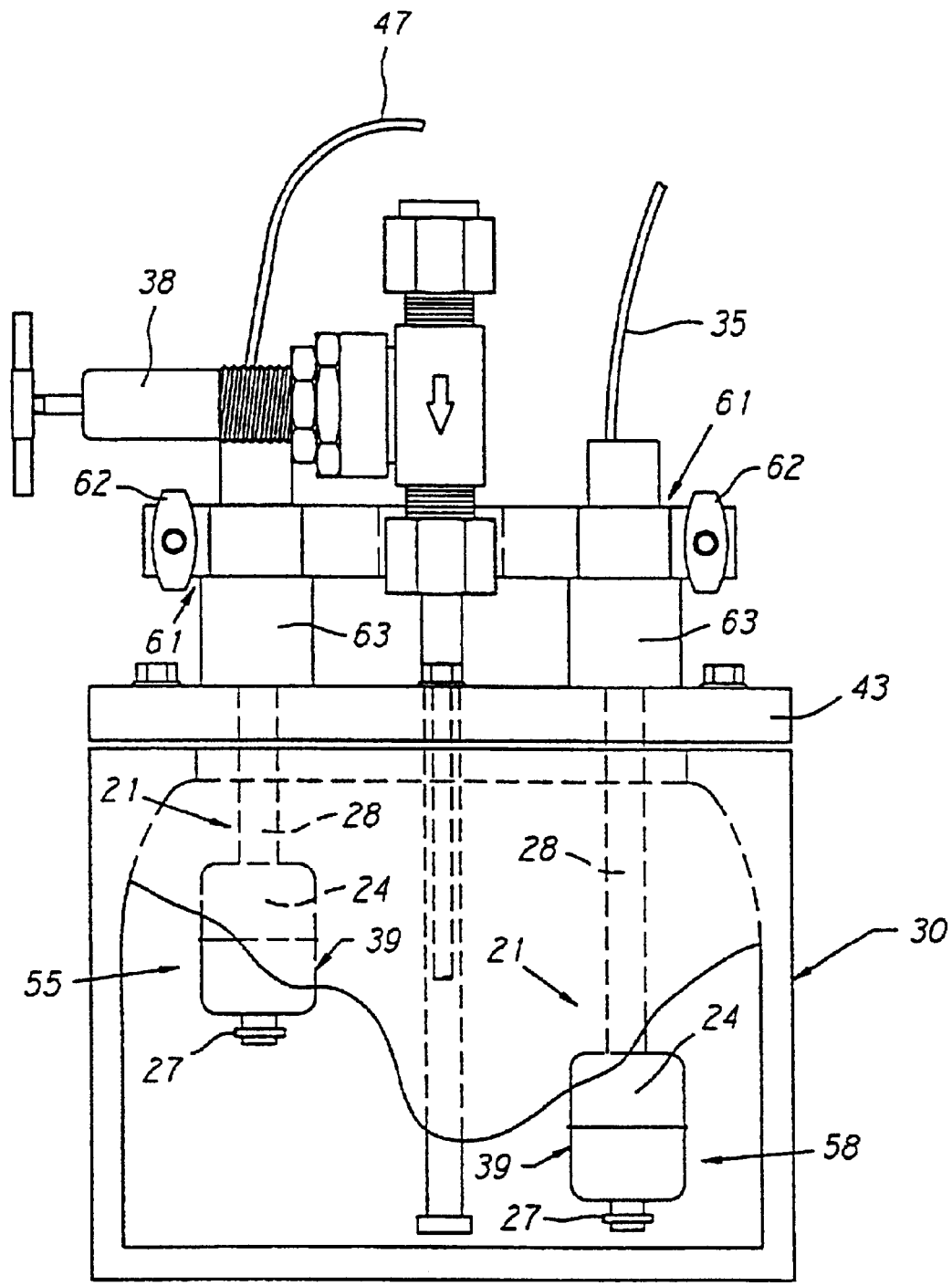
FIG. 8 is a schematic side view in partial cross-section of a refillable ampule according to another embodiment of the present invention.

A particularly preferred refillable ampule 30 is illustrated in FIG. 8. The ampule 30 in FIG. 8 has two metallic level sensor assemblies 21, each comprising a metallic level sensor 39. The first 55 is for detecting high level conditions. As before, preferably metallic level sensor 39 is a dual level sensor as described in FIG. 6. The second 58 detects a low level condition. Low level metallic level sensor 58 is a single level float sensor that signals the CVD reactor, an independent alarm module, or a temperature control unit that the source chemical level with in ampule 30 has reached a low level, terminating normal process operations. Cable 35 carries two wires. These two wires are used to interface with the semiconductor processing equipment. In particular, the two wires are connected across pins 1 and 2 of the interface circuitry depicted in FIG. 13. When the metallic level sensor 39 is employed, pin 3 is left floating.

As is apparent from the above discussion, metallic level sensor assembly 21 can have a number of configurations. FIGS. 9–12 illustrate just a few of the available preferred configurations.

FIG. 9 illustrates a metallic level sensor assembly 21 for refillable ampule 30 comprising a metallic level sensor 39 with two trigger points a "HIGH LEVEL" trigger point 41 and a "HIGH—HIGH" level trigger point 41*a*.

Figure 15A:
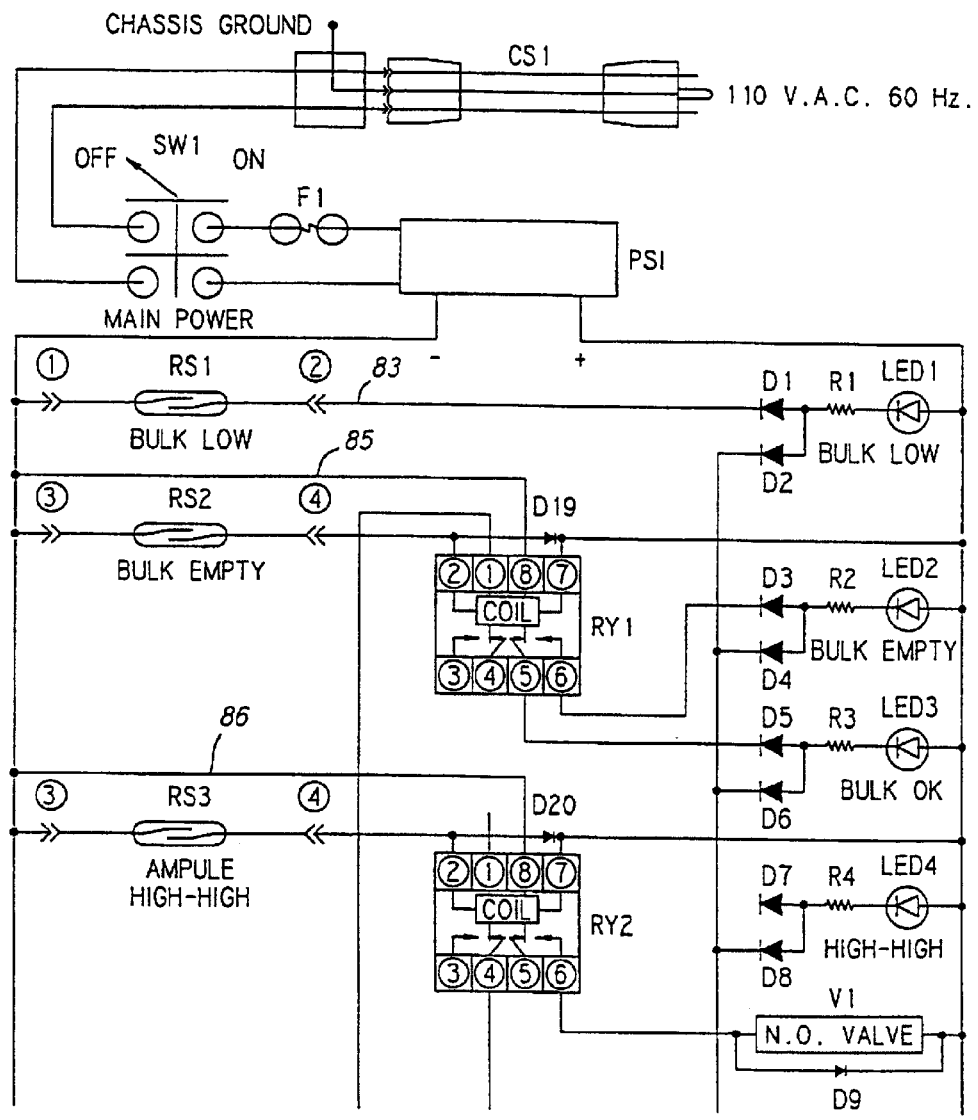
FIGS. 15, 15A and 15B are a schematic diagram of control circuitry for a control unit.
Figures 15, 15A, 15B:
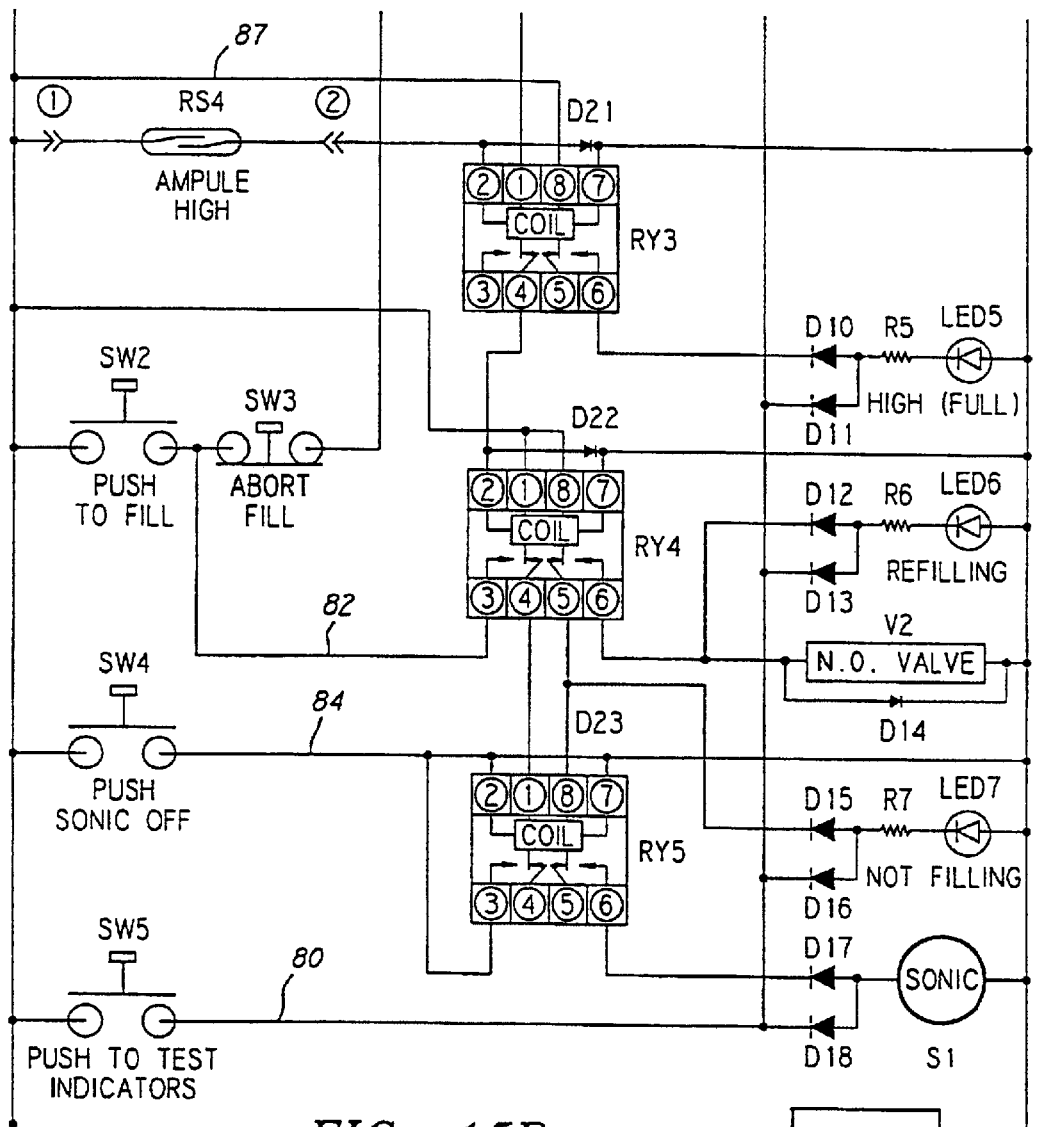

FIG. 10 illustrates a metallic level sensor assembly 21 for refillable ampule 30 comprising two metallic level sensors 39. The first 49 is a dual level sensor as described in FIG. 9. The second 50 detects a low level condition. Low level metallic level sensor 50 is a single level float sensor that signals the CVD reactor, an independent alarm module, or a temperature control unit that the source chemical level with in ampule 30 has reached a low level, terminating normal process operations. High level metallic level sensor 49 is a dual level float sensor with two trigger points a "HIGH LEVEL" trigger point 41 and a "HIGH—HIGH" level trigger point 41*a* as previously described. This configuration has an advantage in that only one hole must be provided in the lid 43 of ampule 30 for the source chemical level sensors, thus reducing the potential for contamination of source chemical. The cable 35 carries six wires. Four of these wires terminate in the control panel as indicated in FIGS. 15, 15A and 15B and two are used to interface with the semiconductor processing equipment. In particular, the two wires are connected across pins 1 and 2 of the interface circuitry depicted in FIG. 13. When the metallic level sensor 39 is employed, pin 3 is left floating.

Figure 11:
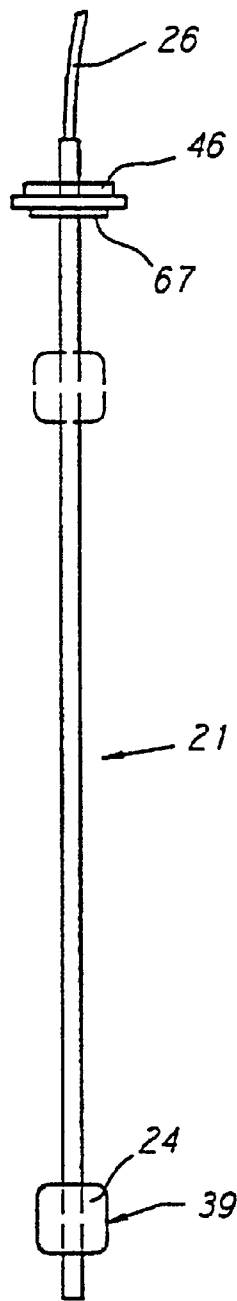
FIG. 11 is a side view of metallic level switch assembly for a bulk container according to one embodiment of the present invention.

FIG. 11 illustrates a metallic level sensor assembly 21 for a bulk container 20 comprising a dual level metallic level sensor 39 with trigger points set at a "BULK EMPTY" trigger point and at a bulk full trigger point. The bulk full trigger point is used by the supplier of the high purity source chemical to fill bulk container 20 after cleaning and servicing the tank.

Figure 12:
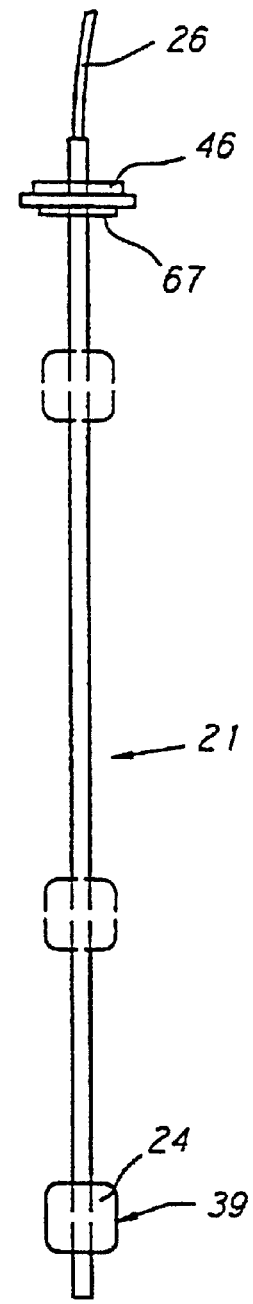
FIG. 12 is a side view of a metallic level switch assembly for a bulk container according to another embodiment of the present invention.

FIG. 12 illustrates a metallic level sensor assembly 21 for a bulk container 20 comprising a triple level metallic level sensor 39 with trigger points set to detect the following level conditions: "BULK EMPTY", "BULK LOW", and "BULK FULL". Again, the bulk full trigger point is used by the supplier to the high purity source chemical to fill bulk container 20 after cleaning and servicing the tank.

The manner in which metallic level sensor assembly 21 is attached to ampule 30 is described in connection with FIGS. 8–12. A ferrule 46 is permanently attached to one end of shaft 28 for attachment of the metallic sensor assembly 21 to ampule 30. Ferrule 46 is preferably constructed from 316L stainless steel, and the preferred method of attachment is welding.

Metallic level sensor assembly 21 is attached to ampule 30 using ferrule 46 in conjunction with clamp 61. Clamp 61 is preferably a flange clamp of the type used for sanitary piping. Clamp 61 is used to clamp flange surface 62 of ferrule 46 against a mating flange surface on a pipe 63 extending out of the top of ampule lid 43. Clamp 61 is tightened around ferrule 46 and the mating flange on pipe 63 by tightening knob 65. A teflon O-ring 67, which is interposed between the mating flange surfaces, is compressed as clamp 61 is tightened, thereby providing leak tight seal.

Alternatively, metallic level sensor assembly 21 can be attached to ampule 30 by welding a threaded connector plug to shaft 28. The threaded connector plug would then be threaded into a mating female connector on lid 43 of ampule 30.

The operation of control unit 40 will now be described in connection with FIGS. 1, 2, 15, 15A and 15B.

Connection to the 110 V.A.C. 60 Hz. Plant Power is made via a standard U-ground male plug of the AC Cord Set CS1. Cord set CS1 plugs into the filter assembly L1. Filter L1 provides line conditioning for both incoming and outgoing transients and connects the AC power to the main power switch SW1. Filter L1 also provides the chassis ground connection.

Main power switch SW1, is a Double Pole Double Throw (DPDT) toggle switch located on the upper left-hand corner of the control panel 52 of the control unit 40. Both the hot and neutral sides of the AC line are switched ON and OFF. Switched AC power is connected to the Fuse F1 through main power switch SW1. Fuse F1 is ¾ AMP, 3 AG size (¼".times.1¼"), standard blow fuse mounted inside control unit 40.

Conditioned, switched, and fused AC power is connected to the AC input of the linear power supply PS1. Power supply PS1 is located inside the control unit 40 and provides regulated 24 V.D.C. power for the control unit 40 circuitry.

The "BULK LOW" circuit 83 will be described first.

When the level of source chemical in bulk container 20 is above the "LOW LEVEL" trigger point, float 24 is floated up and the "BULK LOW" sensor reed switch RS1, is open and the "BULK LOW" indicator LED1 is off. (It should be noted that the reed switches are only shown in representative form as being inside the control panel. In reality the reed switches are in respective containers in the metallic level sensor assemblies 21.)

When the level of product in bulk container 20 goes below the "LOW LEVEL" trigger point, float 24 floats down and the "BULK LOW" sensor reed switch RS1, is closed and the "BULK LOW" indicator LED1 is turned on.

With respect to the "BULK EMPTY" circuit 85, when the level of product in bulk container 20 is above the "EMPTY LEVEL" trigger point, float 24 is floated up and the "BULK EMPTY" sensor reed switch RS2 is open, and the control relay RY1 coil (pins 2 to 7) is deenergized. When RELAY RY1 is deenergized, the normally open contacts (N.O.) (pins 8 to 6), are open, and the "BULK EMPTY" indicator LED2 is off. When relay RY1 is deenergized, the normally closed (N.C.) contacts (pins 8 to 5) are closed and the "BULK OK" indicator LED3 is on. When relay RY1 is deenergized, the N.C. contacts (pins 1 to 4) are closed and the refill circuit is made.

When the level of product in the Bulk Container goes below the "EMPTY LEVEL" trigger point, the float 24 floats down and the "BULK EMPTY" sensor reed switch RS2 is closed, and the control relay RY1 coil (pins 2 to 7) is energized. When relay RY1 is energized, the N.O. contacts (pins 8 to 6) close and the "BULK EMPTY" indicator LED2 is turned on. When relay RY1 is energized, the N.C. contacts (pins 8 to 5) open and the "BULK OK" indicator LED3 is turned off. When relay RY1 is energized, the N.C. contacts (pins 1 to 4) open and the refill circuit is broken.

The ampule "HIGH—HIGH LEVEL" circuit 86 is now described.

When the level of product in the ampule 30 is below the "HIGH—HIGH LEVEL", the float 24 of dual level metallic level sensor 39 is floated down with respect to the "HIGH—HIGH LEVEL" trigger point 41a, and the ampule 30 "HIGH—HIGH" sensor reed switch RS3 is open. Thus, the control relay RY2 coil (pins 2 to 7) is deenergized. When relay RY2 is deenergized, the N.O. contacts (pins 8 to 6) are open and the "AMPULE HIGH—HIGH" indicator LED4 is off. When relay RY2 is deenergized, the N.O. contacts (pins 8 to 6) are open and the N.O. coil of air control valve V1 is deenergized and valve V1 is open. When relay RY2 is deenergized, the N.C. contacts (pins 1 to 4) are closed and the refill circuit is made.

When the level of product in ampule 30 goes above the "HIGH—HIGH LEVEL" trigger point 41a, the float 24 of dual level metallic level sensor 39 floats up with respect to the "HIGH—HIGH LEVEL" trigger point 41a, and the ampule 30 "HIGH—HIGH" sensor reed switch RS3 is closed. Thus, control relay RY2 Coil (pins 2 to 7) is energized. When relay RY2 is energized, the N.O. contacts (pins 8 to 6) close and the "AMPULE HIGH—HIGH" indicator LED4 is turned on. When relay RY2 is energized, the N.O. contacts (pins 8 to 6) close and the N.O. coil of control solenoid valve V1 is energized and valve V1 closes, stopping the refill cycle. When relay RY2 is energized, the N.C. contacts (pins 1 to 4) open and the refill circuit is broken.

With respect to the "AMPULE HIGH" circuit 87, when the level of product in ampule 30 is below the "HIGH LEVEL" trigger point 41, the float of dual level float sensor 39 is floated down with respect to the "HIGH LEVEL" trigger point 41, and the "AMPULE HIGH" sensor reed switch RS4 is open. Thus, the control relay RY3 coil (pins 2 to 7) is deenergized. When relay RY3 is deenergized, the N.O. contacts (pins 8 to 6) are open and the "AMPULE HIGH" indicator LED5 is off. When relay RY3 is deenergized, the N.C. contacts (pins 1 to 4) are closed and the refill circuit is made.

When the level of source chemical in the ampule 30 goes to or above the "HIGH LEVEL" trigger point 41, the float 24 of dual level metallic level sensor 39 floats up and the "AMPULE HIGH" sensor reed switch RS4, is closed and the control relay RY3 coil (pins 2 to 7) is energized. When relay RY3 is energized, the N.O. contacts (pins 8 to 6) close and the "AMPULE HIGH" indicator LED5 is turned on. When relay RY3 is energized, the N.C. contacts (pins 1 to 4) open and the refill circuit is broken.

Refill circuit 82 is now described. Before the refill cycle begins, the "PUSH TO FILL" switch SW2 is open, the "ABORT FILL" switch SW3 is closed, the control relay RY4 coil (pins 2 to 7) is deenergized, the N.C. contacts (pins 8 to 5) are closed and the "AMPULE NOT FILLING" indicator LED7 is on, the N.O. contacts (pins 8 to 6) are open and the "AMPULE REFILLING" indicator LED6 is off, the N.O. contacts (pins 8 to 6) are open and the N.C. coil of air control valve V2 is deenergized, and solenoid valve 12 is closed. When the N.C. solenoid valve V2 is closed, there is no control pressure supplied to pneumatic valve 42 through passage 40.

To start the refill cycle, the "PUSH TO FILL" switch SW2 is momentarily pushed closed, the coil of control relay RY4 (pins 2 to 7) is energized through the N.C. contacts of SW3, RY1 (pins 1 to 4), RY2 (pins 1 to 4), RY3 (pins 1 to 4). As RY4 energizes, N.O. contacts (pins 1 to 3) close. This energizes relay RY4 and latches it in the energized state. "PUSH TO FILL" switch SW2 may now be released.

The refill cycle continues with RY4 energized, the N.C. contacts (pins 8 to 5) are open and the "AMPULE NOT FILLING" indicator LED7 is turned OFF. Also, the N.O. contacts (pins 8 to 6) are closed, and the "AMPULE REFILLING" indicator LED6 is turned on. Finally, the N.O. contacts (pins 8 to 6) are closed and the N.C. solenoid valve V2 is energized and the valve is opened. When the N.C. solenoid valve V2 is opened, control pressure is supplied through passage 46 to pneumatic valve 42, opening pneumatic valve 42. Source chemical from bulk container 20 can now flow through refill line 44 to ampule 30.

The end of the refill cycle occurs in one of six (6) ways:

MODE 1: Control pressure failure: Pneumatic valve 42 closes, ending the refill cycle.

MODE 2: Power Failure: The N.C. solenoid valve V2 is de-energized and solenoid valve V2 is closed. When the N.C. solenoid valve V2 is closed, no control pressure is supplied through passage 46 to pneumatic valve 42. Thus, pneumatic valve 42 closes, ending the refill cycle.

MODE 3: ABORT FILL: If an operator presses the "ABORT FILL" switch SW3, which is a push-button switch, the refill circuit 82 is broken. Control relay RY4 de-energizes, N.O. contacts (pins 8 to 6) open, and N.C. solenoid valve V2 is de-energized, cutting off the flow of control pressure to pneumatic valve 42 and ending the refill cycle.

MODE 4: BULK EMPTY: If the level of product in the bulk container 20 goes below the "EMPTY LEVEL" trigger point, the float of dual level float sensor 24 floats down with respect to the "EMPTY LEVEL" trigger point, and the "BULK EMPTY" sensor reed switch RS2 closes. As a result, the control relay RY1 coil (pins 2 to 7) is energized, N.C. contacts (pins 1 to 4) open, and the refill circuit 82 is broken. This causes control relay RY4 to de-energize, N.O. contacts (pins 8 to 6) to open, and N.C. solenoid valve V2 is de-energized, closing solenoid valve V2. When the N.C. solenoid valve V2 closes, no control pressure is supplied through passage 46 to pneumatic valve 42. Thus, pneumatic valve 42 closes, ending the refill cycle.

MODE 5: AMPULE HIGH—HIGH: If the level of source chemical in ampule 30 goes above the "HIGH—HIGH LEVEL" trigger point 41a, the float of dual level float sensor 39 floats up with respect to the "HIGH—HIGH LEVEL" trigger point 41a, and the "HIGH—HIGH" sensor reed switch RS3 closes. In turn, the coil of control relay RY2 (pins 2 to 7) is energized, the N.O. contacts (pins 8 to 6) close, and the N.O. solenoid valve V1 is energized, closing the valve. When the N.O. solenoid valve V1 is closed, no control pressure can be supplied through passage 46 to pneumatic valve 42, thus ending the refill cycle. Additionally, when relay RY2 is energized, the N.C. contacts (pins 1 to 4) open, and the refill circuit 82 is broken. As a result, control relay RY4 de-energizes, N.O. contacts (pins 8 to 6) open, N.C. solenoid valve V2 is de-energized, causing solenoid valve V2 to close. When N.C. solenoid valve V2 is closed, no control pressure can be supplied through passage 46 to pneumatic valve 42, thus ending the refill cycle.

MODE 6: AMPULE HIGH: If the level of source chemical in the ampule 30 goes to or above the "HIGH LEVEL" trigger point 41, the float of dual level float sensor 39 floats up with respect to "HIGH LEVEL" trigger point 41, and the "AMPULE HIGH" sensor reed switch RS4 closes. In turn, the coil of control relay RY3 (pins 2 to 7) is energized. When relay RY3 is energized, the N.C. contacts (pins 1 to 4) open, and the refill circuit 82 is broken. As a result, control relay RY4 deenergizes, N.O. contacts (pins 8 to 6) open, N.C. solenoid valve V2 is de-energized, causing the valve to close. When the N.C. solenoid valve V2 is closed, no control pressure is supplied to pneumatic valve 42, ending the refill cycle.

Sonic circuit 84 is now described in connection with FIGS. 2, 15, 15A, and 15B. When the "MAIN POWER" switch SW1 is first turned ON, the sonic circuit 84 will self-test and an audible signal will be heard. The sonic transducer S1 is powered by the circuit through the N.C. contacts (pins 8 to 5) of relay RY4, through the N.C. contacts (pins 8 to 5) of relay RY5, and through Diode D17. The Operator presses the "PUSH SONIC OFF" switch SW4 to silence the audible signal.

When the "PUSH SONIC OFF" switch SW4 is momentarily closed, the Control relay RY5 coil (pins 2 to 7) is energized. As a result, N.C. contacts (pins 8 to 5) open, and the audible signal is turned off. Also, N.O. contacts (pins 1 to 3) close. When relay RY5 is energized, N.O. contacts (pins 1 to 3) are latched. "PUSH SONIC OFF" switch SW4 may now be released and the audible signal will stay off.

At the start of the refill cycle, control relay RY4 energizes. In turn, N.C. contacts (pins 1 to 4) and N.C. contacts (pins 8 to 5) open, de-energizing and un-latching control relay RY5 and simultaneously removing power from the contacts of RY5 connected to the sonic transducer S1. Therefore, the audible signal still remains off.

At the end of the refill cycle, control relay RY4 de-energizes. In addition, N.C. contacts (pins 8 to 5) close and, through the N.C. contacts (pins 8 to 5) of RY5, energize the sonic transducer Si so that a audible signal is sounded.

At the Operator's discretion, the Sonic audible signal may be silenced by pressing the "PUSH SONIC OFF" switch SW4. When SW4 momentarily closes, control relay RY5 energizes and latches as described above. In turn, N.C. contacts (pins 8 to 5) open and de-energize the sonic transducer S1. Also, N.O. contacts (pins 1 to 3) close, energizing and latching relay RY5 in the energized state. "PUSH SONIC OFF" switch SW4 may now be released and the audible signal will stay OFF until the next refill cycle ends.

When the "PUSH TO TEST INDICATORS" switch SW5 is momentarily pressed, test circuit 86 is completed and power is connected to LED1, LED2, LED3, LED4, LED5, LED6, LED7, and sonic transducer S1, thus energizing all of these indicators.

Each Diode anode of test circuit 86 is connected in parallel to the direct drive Diode anode of the various indicator circuits. This blocks any potential false circuit paths.

Diodes D9, D14, D19, D20, D22, D23 are connected in parallel across their respective relay coils with their cathodes toward the positive power supply line. When a coil that has been energized is deenergized, the magnetic field that is created, quickly collapses and creates a transient voltage of opposite polarity to the energizing voltage across the coil terminals. Diodes D9, D14, D19, D20, D22, D23 provides a discharge path in its forward biased direction for this transient voltage and dissipates the stored energy. This configuration tends to protect the contacts of the switch that energizes the coil from high voltage spikes that may cause arc damage and also contributes to a quieter overall electrical environment.

Figure 16:
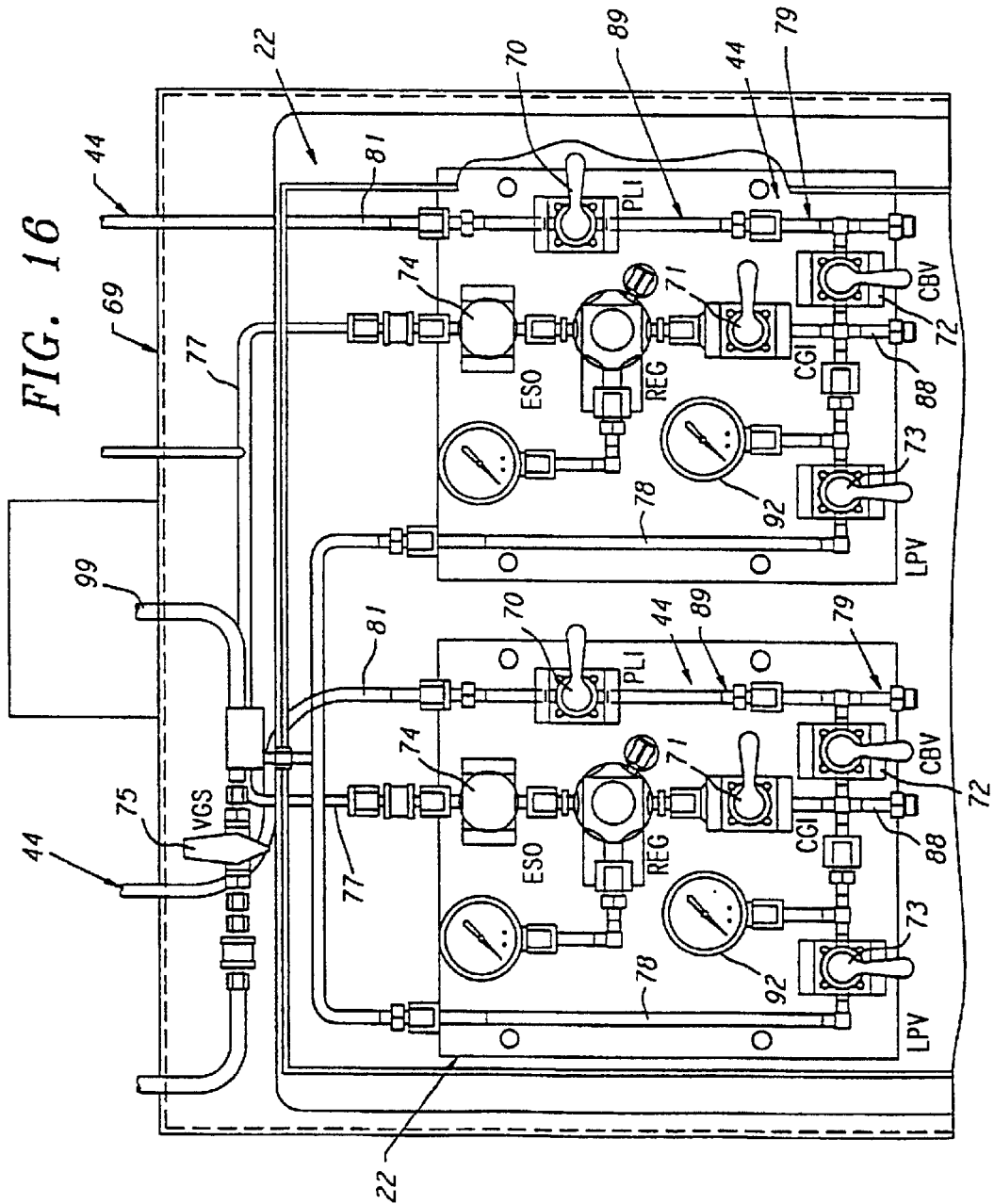
FIG. 16 is a front view of a manifold layout according to one embodiment of the present invention.

FIG. 16 illustrates a partial view of a chemical cabinet 69 having two manifolds 22 therein. Each manifold 22 connects up to a separate bulk container 20. Manifold 22 contains six valves: process isolation valve 70, carrier gas isolation valve 71, container bypass valve 72, low pressure vent valve 73, emergency shut off valve 74, and vacuum supply valve 75. Obviously chemical cabinet 69 can have one or more manifolds in it depending on process requirements.

Figure 17:
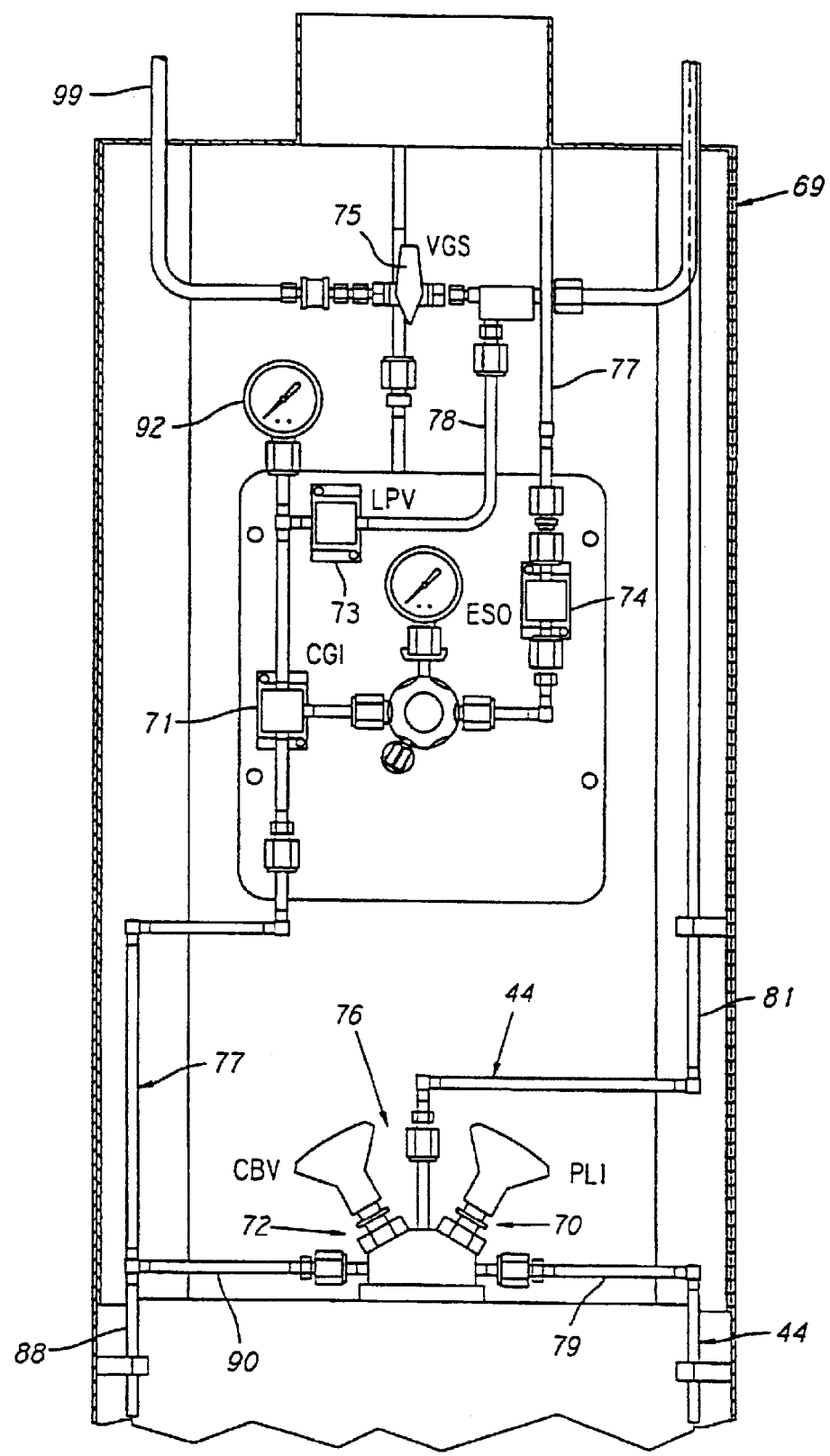
FIG. 17 is a front view of a manifold layout for an embodiment of the present invention.
Figure 48:
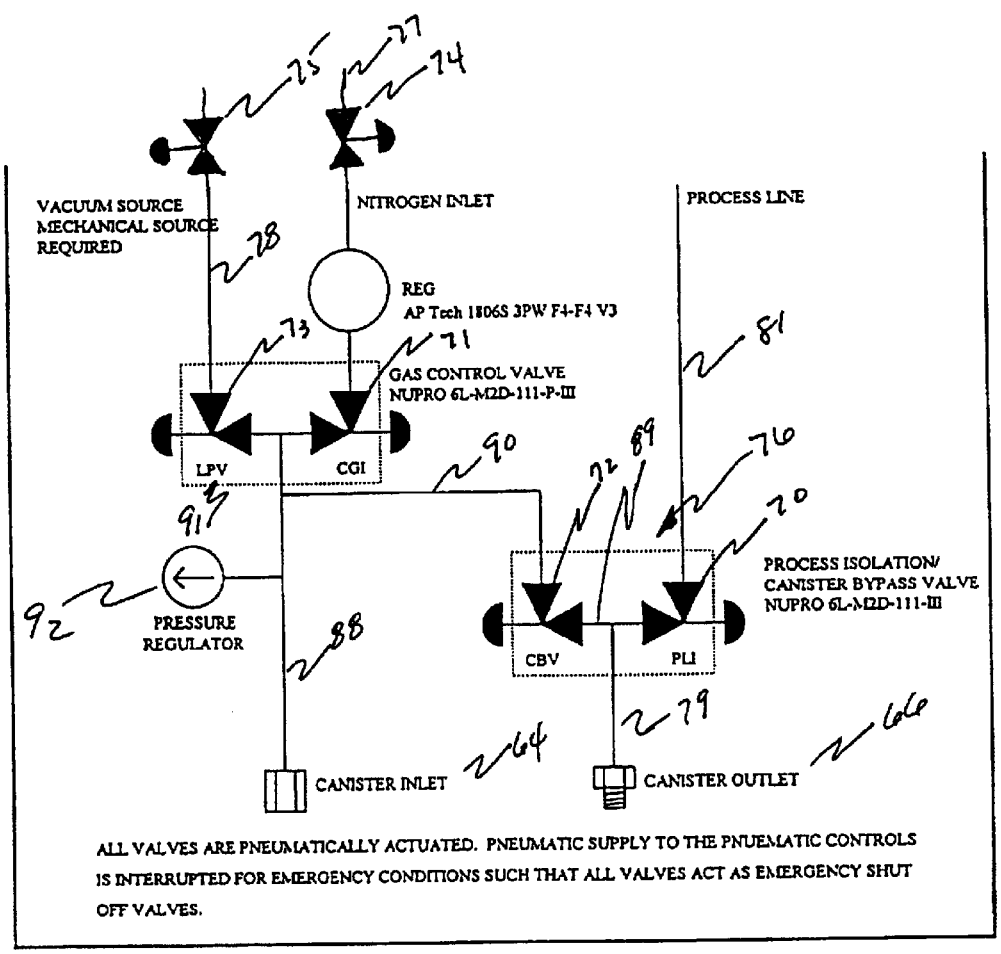

A particularly preferred manifold arrangement is depicted in FIG. 17. The difference between the manifold in FIG. 16 and the one in FIG. 17 is that a block valve 76 contains both a container bypass valve 72 and a refill line isolation valve 70. Thus, block valve 76 is substituted for separate valves 70 and 72 of FIG. 16. As a result of this modification, high purity source chemical is prevented from being trapped in the passage 89 of refill line 44 illustrated in FIG. 16. This is because passage 89 is effectively removed from the manifold with the use of block valve 76. Thus, the manifold configuration of FIG. 17 further reduces the risk of introducing contamination to the system.

A most preferred embodiment of manifold 22 is depicted in FIG. 18. In this embodiment, in addition to employing a process isolation block valve 76 for the canister bypass valve 72 and the process line isolation valve 70, a vacuum/pressure block valve 91 is used for the low pressure vent valve 73 and the carrier gas isolation valve 71. Again, as with the embodiment depicted in FIG. 17, the basic operation of the manifolds are the same. Thus, the description of the operation of the manifold for various processes applies to all three depicted embodiments.

Manifold 22 is preferably used to isolate the refill line 44 when the bulk container 20 is replaced with a fresh tank. This helps prevent contamination of the system. Thus, the preferred manifold 22, is not required for operation of refill system 18. Naturally, if a manifold is not used, bulk canister input valve 66 will need to be attached to a regulated source of inert gas and bulk canister output valve 64 will need to be connected to refill line 44.

Process isolation valve 70 is interposed in refill line 44 between the inlet valve 38 of ampule 30 and the outlet valve 66 of bulk container 20. When process isolation valve 70 is closed, the portion of process line 44 down stream from valve 70 is isolated from the atmosphere during subsequent replacement of bulk tank 20. Carrier gas isolation valve 71 is interposed in carrier gas line 77 between the inlet valve 64 of bulk container 20 and the carrier gas supply source.

Low pressure vent valve 73 is interposed in vacuum line 78, which is communicated to both the carrier gas line 77 and refill line 44. Container bypass valve 72, however, is interposed in the line between refill line 44 and low pressure valve 73. This line is both pressurized or evacuated dependent on the states of LPV and CGI.

Emergency shut off valve 74 is a normally closed valve, preferably a pneumatic valve. Thus, any loss in system air pressure will immediately close the valve. Typically emergency shut off valve 74 is controlled by the facility emergency gas pad shut off control system. The use of pneumatically activated normally closed valves in the manifold and on the bulk canister inlet and outlet enables all valves to act as emergency shut-off valves. Thus, when the ESO condition is activated, the pneumatic supply to the valves will be cut off, closing all valves. Vacuum supply valve 75 is disposed in a venturi loop 99 so that when it is opened, vacuum is supplied to vacuum supply lines 78.

During normal operation the manifold 22 is left in the delivery configuration. Pneumatic valve 42 in the refill line 44 is used to control the refilling operation. In the delivery configuration the emergency shutoff valve 74 is open, the carrier gas isolation valve 71 is open, the process line isolation valve 70 is open, the vacuum gas shutoff valve 75 is closed, the low pressure vent valve 73 is closed, the new canister bypass valve 72 is closed, the bulk canister inlet valve 64 is open and the bulk canister outlet valve 66 is open.

To change the bulk canister 20, the following preferred procedure is used to prevent contamination of the high purity chemical being delivered. First the high purity chemical must be evacuated from the manifold and the bulk canister 20 depressurized and isolated. Next the manifold should be purged. After purging, the depleted bulk canister should be disconnected and removed. Then the new full bulk canister 20 should be installed and connected. The connections for the full bulk canister should be tested for leaks. The manifold should then be purged and the new bulk canister 20 placed in service.

To evacuate the high purity chemical remaining in the manifold 22 and to isolate, depressurize and shut off the bulk canister 20, the following procedure is presently preferred. (It should be noted that unless otherwise expressly noted, the emergency shutoff valve 74 should open throughout all of the following procedures.) Ensure that the canister bypass valve 72 is closed, which it should be in the delivery configuration. Then close the process line isolation valve 70. Next close the bulk canister outlet valve 66. Close the carrier gas isolation valve 71 and open the vacuum gas shutoff valve 75 and the low pressure vent valve 73. Wait until the manifold pressure gauge 92 reads approximately zero psia, which takes approximately four minutes.

Close the bulk canister inlet valve 64. Close the low pressure vent valve 73 and open the carrier gas isolation valve 71 and the canister bypass valve 72. Open the canister outlet valve 66 and wait approximately a half a minute or until the bulk canister pressure equalizes with the pressurizing gas. Close the bulk container bypass valve 72, the bulk canister outlet valve 66 and the carrier gas isolation valve 71. Open the bulk canister inlet valve 64. The foregoing steps should preferably be repeated a number of times, most preferably a minimum of five times. Finally the bulk canister inlet valve 64 should be closed.

To purge the manifold prior to disconnecting the depleted canister 20, the following steps should preferably be followed. Open the canister bypass valve 72 and the low pressure vent valve 73. Wait approximately 30 seconds to maximize the evaporation of the residual high purity chemical in the manifold. Close the low pressure vent valve 73 and open the carrier gas isolation valve 71. Wait approximately 4 seconds and then close the carrier gas isolation valve 71. Open the low pressure vent valve for approximately 10 seconds and then close it again. Repeat the steps of closing the low pressure vent valve 73; opening the carrier gas isolation valve 71; waiting approximately 4 seconds and then closing the carrier gas isolation valve 71; and, opening the low pressure vent valve for approximately 10 seconds and then closing it again preferably a minimum of nineteen times. Then close the vacuum gas shutoff valve 75 and wait approximately three seconds. Then open the low pressure vent valve 73 for approximately five seconds.

To disconnect and remove the depleted bulk canister 20, the following steps are preferred. Open the carrier gas isolation valve 71 to keep a positive pressure of the pressurizing gas, preferably helium, on the manifold. Open the canister inlet and outlet valves 64 and 66. With a suitable tool, support the canister outlet valve 66 to prevent rotation, and then loosen the canister outlet valve 66 connection and disconnect the canister outlet tubing 79. In a similar fashion, disconnect the canister inlet tubing 88. The pressurizing gas should be flowing freely out of the canister inlet and outlet tubing 88 and 79 throughout the operation and until the new canister is connected. This prevents atmospheric contamination of the manifold. Disconnect the level sensor cable, unfasten the safety chains and straps and carefully remove the depleted bulk canister 20 from the enclosure.

To install a full bulk canister 20, the following steps should preferably be performed. Carefully place the bulk canister in the enclosure and reconnect the safety strap and chain. Connect the canister inlet valve 66 and outlet valve 64 connections to the outlet and inlet tubing 88 and 79 reversing the procedure used to disconnect them from the depleted bulk canister 20. Connect the level sensor cable and close the carrier gas isolation valve 71.

Before moving to the next step, a test for leakage should be performed. Open the vacuum gas shutoff valve 75 and the low pressure vent valve 73. After approximately 10 seconds, close the low pressure vent valve 73 and open the carrier gas isolation valve 71. After a few seconds, preferably four, close the carrier gas isolation valve 71 and the vacuum gas shutoff valve 75. Using an appropriate leak tester, check the inlet and outlet canister connections for leaks. If none appear, the manifold should be purged and then set for normal operation.

To purge the manifold, with the canister inlet and outlet valves 64 and 66 closed, the canister bypass valve 72, the vacuum gas shutoff valve 75 and the low pressure vent valve 73 should first be opened. After approximately 10 seconds, the low pressure vent valve 73 should be closed. Open the carrier gas isolation valve 71 for approximately four seconds and then close it. Repeat the opening and closing of the low pressure vent valve 73 and the carrier gas isolation valve 71 preferably a minimum of nineteen times. Open the low pressure vent valve 73 for approximately 15 seconds to ensure that vacuum has been pulled on the manifold and then close it. Close the vacuum gas shutoff valve 75 and the carrier bypass valve 72.

To place the manifold 22 in the normal operating configuration, slowly open the carrier gas isolation valve 71. Then slowly open the canister inlet valve 64 and then the canister outlet valve 66. Adjust the pressure regulator to the desired delivery pressure and open the process line isolation valve 70.

In addition, the manifold 22 can be used to purge and evacuate the refill line 44 as well. To accomplish this, the purge and evacuation cycles would be performed with the process line isolation valve open and the pneumatic valve 42 closed. Also, if desired, additional parts of the system can be evacuated and purged by merely opening downstream valves to the final point that is desired to be purged. The suggested times for purging and evacuating should be extended to allow for the vacuum to be completely pulled on the lines being evacuated and purged.

While the bulk chemical refill system of the present invention has been described in connection with high purity TEOS, the system has application with many other high purity source chemicals, as a person of ordinary skill in the art would recognize. A non-exclusive list of the various high purity source chemical that might be used in the chemical refill system of the present invention is contained in Table 1.

TABLE 1

Aluminum Tri-sec-Butoxide
Borazine
Carbon Tetrachloride
Chloroform
Dichloroethylene
Dichloromethane
Diethylsilane
Isopropoxide
Hexafluoroacetylacetonate-
Copper (I)-Trimethylphosphine
Silicon Tetrachloride
Tetrakis (Diethylamino) titanium
Triethylphosphite
Titanium Tetrachloride
Trimethylorthosilicate
Tetramethylcyclotetrasiloxane
Trichloroethane
Trimethylphosphite
Trimethylborate
Titanium N-Butoxide
Titanium
Tantalum Ethoxide
Triethylborate
Triethylphosphate
Trimethylphosphate
Titanium Ethoxide
Titanium N-propoxide
Titanium Isobutoxide
Tris (Trimethylsiloxy) Boron
Tris (Trimethylsilyl) Phosphate Although the present invention has been described in detail, it should be understood that various changes, substitutions and alterations can be made hereto without departing from the spirit and scope of the invention as described by the appended claims.

What is claimed is:

1. A system comprising:
a first container having a first inlet port, a first outlet port, and a first level sensor for generating a low level signal and a high level signal;
a second container having a second inlet port, a second outlet port, and a second level sensor for generating a low level signal;
a refill line removably coupled to the first inlet port and the second outlet port;
an inert gas pressure source coupled to an interior of the second container;
a control unit coupled to the first level sensor, the second level sensor and a first valve in said refill line, the first valve to allow the transfer of high purity chemicals to the first container in response to the control unit receiving the low level signal from the first level sensor and to terminate the transfer of high purity chemicals in response to said control unit receiving the high level signal from the first level sensor; and
a manifold, comprising:
a carrier gas line for providing inert gas from the inert gas pressure source to the second container;
a second valve disposed within said refill line to isolate the second outlet port from a portion of the refill line;
a third valve disposed within said carrier gas line isolate said inert gas pressure source from the second inlet port;
means for connecting a vacuum source to said carrier gas line; and
means for bypassing said inert gas pressure source and the vacuum source to at least a portion of said refill line not isolated by said second valve.

2. A system as in claim 1 wherein the first container comprises stainless steel.

3. A system as in claim 2 wherein the second container comprises stainless steel.

4. A system as in claim 1 wherein the first valve is a normally closed pneumatic valve.

5. A system as in claim 1 wherein the second container further comprises an inlet pneumatic valve integral with the second inlet port.

6. A system as in claim 1 wherein the second container further comprises an outlet pneumatic valve integral with the second outlet port.

7. A system as in claim 1 wherein the first level sensor is a stainless steel metal float sensor.

8. A system as in claim 1 wherein the second level sensor is a stainless steel metal float sensor.

9. A method of refilling the first container using the system of claim 1 comprising:
pressurizing the second container with an inert gas;
opening the first valve to permit the transfer of high purity chemical from the second container to the first container in response to the control unit receiving a low level signal from the first level sensor; and
closing the first valve to terminate the transfer of high purity chemical from the second container to the first container in response to the control unit receiving a high level signal from the first level sensor.

10. A high purity chemical refill system, comprising:
a first container for storing high purity chemicals, comprising an inlet port, an outlet port, and a first level sensor disposed within the first container and generating at least a low level signal and a high level signal;
a second container for storing high purity chemicals, comprising an inlet port, an outlet port and a second level sensor disposed within the second container and generating at least a low level signal;
a refill line removably connectable to the inlet port of the first container and to the outlet port of the second container;
a first valve in the refill line;
an inert gas pressure source communicating with the interior of the second container;
a control unit electrically communicating with the first level sensor, the second level sensor and the first valve, wherein the first valve is opened to permit transfer of high purity chemicals to the first container in response to the control unit receiving the low level signal from the first level sensor and the first valve is closed to terminate the transfer of high purity chemicals in response to the control unit receiving the high level signal from the first level sensor and
a manifold comprising:
a process line isolation valve in the refill line to isolate the second container from a portion of the refill line;
a carrier gas isolation valve for isolating the second container from the inert gas pressure source;
a low pressure vent valve in the carrier gas line; and
a container bypass valve in the refill line.

11. A high purity chemical refill system as in claim 10 wherein the first container comprises stainless steel.

12. A high purity chemical refill system as in claim 11 wherein the second container comprises stainless steel.

13. A high purity chemical refill system as in claim 10 wherein the first valve is a normally closed pneumatic valve.

14. A high purity chemical refill system as in claim 10 wherein the second container further comprises an inlet pneumatic valve integral with the inlet port.

15. A high purity chemical refill system as in claim 10 wherein the second container further comprises an outlet pneumatic valve integral with the outlet port.

16. A high purity chemical refill system as in claim 10 wherein the first level sensor is a stainless steel metal float sensor.

17. A high purity chemical refill system as in claim 10 wherein the second level sensor is a stainless steel metal float sensor.

18. A method of refilling the first container using the high purity chemical refill system of claim 10 comprising:

pressurizing the second container with an inert gas;

opening the first valve to permit the transfer of high purity chemical from the second container to the first container in response to the control unit receiving a low level signal from the first level sensor; and closing the first valve to terminate the transfer of high purity chemical from the second container to the first container in response to the control unit receiving a high level signal from the first level sensor.

\* \* \* \* \*